(12) United States Patent
Herz et al.

(10) Patent No.: US 7,528,292 B2
(45) Date of Patent: May 5, 2009

(54) PLASTID TRANSFORMATION USING MODULAR VECTORS

(75) Inventors: Stefan Herz, München (DE);
Hans-Ulrich Koop, München (DE);
Timothy J. Golds, Freising (DE);
Christian Eibl, Ismaning (DE)

(73) Assignee: Icon Genetics GmbH, Munich (DE)

( * ) Notice: Subject to any disclaimer, the term of this patent is extended or adjusted under 35 U.S.C. 154(b) by 202 days.

(21) Appl. No.: 10/523,474

(22) PCT Filed: Aug. 1, 2003

(86) PCT No.: PCT/EP03/08549

§ 371 (c)(1),
(2), (4) Date: Sep. 6, 2005

(87) PCT Pub. No.: WO2004/015115

PCT Pub. Date: Feb. 19, 2004

(65) Prior Publication Data

US 2006/0117400 A1    Jun. 1, 2006

(30) Foreign Application Priority Data

Aug. 6, 2002 (DE) .............................. 102 36 001

(51) Int. Cl.
*A01H 5/00* (2006.01)
*A01H 5/10* (2006.01)
*C12N 15/82* (2006.01)

(52) U.S. Cl. .................. 800/278; 800/298; 536/23.1

(58) Field of Classification Search ................... None
See application file for complete search history.

(56) References Cited

U.S. PATENT DOCUMENTS 5,451,513 A * 9/1995 Maliga et al. ............... 800/278

FOREIGN PATENT DOCUMENTS

| WO | WO 99/29837 | | 6/1999 |
|---|---|---|---|
| WO | WO 02/055651 | * | 7/2002 |
| WO | WO 02/057466 | A | 7/2002 |
| WO | WO 03/054189 | | 7/2003 |
| WO | WO 03/054201 | | 7/2003 |

OTHER PUBLICATIONS

Staub, J., et al., "Extrachromosomal elements in tobacco plastids,"*Proc. Natl. Acad. Sci. USA*, Aug. 1994, pp. 7468-7472, vol. 91.
Drescher, A., et al., "The Two Largest Chloroplast Genome-encoded Open Reading Frames of Higher Plants are Essential Genes," *Plant J.*, 2000, vol. 22(2), pp. 97-104.
Sikdar, S., et al., "Plastid Transformation in *Arabidopsis thaliana*," *Plant Cell Reports*, 1998, vol. 18, pp. 20-24, Springer-Verlag.
Svab, Z. and P. Maliga, "High-frequency Plastid Transformation in Tobacco by Selection for a Chimeric *aadA* Gene," *Proc. Natl. Acad. Sci. of USA*, 1993, vol. 90, pp. 913-917.
Zoubenko, O., et al., "Efficient Targeting of Foreign Genes Into the Tobacco Plastid Genome," *Nucleic Acids Research*, 1994, vol. 22(19), pp. 3819-3824, Oxford University Press, Surrey, GB.

* cited by examiner

*Primary Examiner*—Anne R Kubelik
(74) *Attorney, Agent, or Firm*—Alston & Bird LLP

(57) ABSTRACT

The invention provides processes for generating transgenic plants or plant cells transformed on their plastome, comprising introducing into plant plastids a first and a second DNA molecule, wherein the first DNA molecule contains a first region homologous to a region of the plastome for directing plastome integration and a first sequence of interest, and the second DNA molecule contains a second region homologous to a region of the plastome and a second sequence of interest, whereby a sequence segment of the first sequence of interest is homologous to a sequence segment of the second sequence of interest, and selecting transformants having an integration sequence stably integrated in the plastome, whereby the integration sequence contains at least a portion of the first and second sequences of interest as a continuous sequence. The invention further provides plant cells, plants, and seeds of plants produced by such processes.

23 Claims, 12 Drawing Sheets

SEQUENCE LISTING

<160> NUMBER OF SEQ ID NOS: 39

<210> SEQ ID NO 1
<211> LENGTH: 21
<212> TYPE: DNA
<213> ORGANISM: Artificial Sequence
<220> FEATURE:
<223> OTHER INFORMATION: PCR primer

<400> SEQUENCE: 1
cactacattt cgctcatcgc c                                              21

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
tattccgact tccccagagc                                                20

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
ctatcagagg tagttggcgt c                                              21

<210> SEQ ID NO 4
<211> LENGTH: 17
<212> TYPE: DNA
<213> ORGANISM: Artificial Sequence
<220> FEATURE:
<223> OTHER INFORMATION: PCR primer

<400> SEQUENCE: 4
ggcatcagag cagattg                                                   17

<210> SEQ ID NO 5
<211> LENGTH: 35
<212> TYPE: DNA
<213> ORGANISM: Artificial Sequence
<220> FEATURE:
<223> OTHER INFORMATION: PCR primer

<400> SEQUENCE: 5
tggagctcga attgccgcga gcaaagatat taatg                               35

<210> SEQ ID NO 6
<211> LENGTH: 30
<212> TYPE: DNA
<213> ORGANISM: Artificial Sequence
<220> FEATURE:
<223> OTHER INFORMATION: PCR primer

<400> SEQUENCE: 6
tacgaattca agagaaggtc acggcgagac                                     30

<210> SEQ ID NO 7
<211> LENGTH: 30
<212> TYPE: DNA
<213> ORGANISM: Artificial Sequence
<220> FEATURE:
<223> OTHER INFORMATION: PCR primer

<400> SEQUENCE: 7
gaccctgcag gcaaaaaatc tcaaatagcc                                     30

<210> SEQ ID NO 8
<211> LENGTH: 28

```
<212> TYPE: DNA
<213> ORGANISM: Artificial Sequence
<220> FEATURE:
<223> OTHER INFORMATION: PCR primer

<400> SEQUENCE: 8
cgggatccga ttttctttta gacttcgg                                        28

<210> SEQ ID NO 9
<211> LENGTH: 28
<212> TYPE: DNA
<213> ORGANISM: Artificial Sequence
<220> FEATURE:
<223> OTHER INFORMATION: PCR primer

<400> SEQUENCE: 9
cgggatccga ttttctttta gacttcgg                                        28

<210> SEQ ID NO 10
<211> LENGTH: 49
<212> TYPE: DNA
<213> ORGANISM: Artificial Sequence
<220> FEATURE:
<223> OTHER INFORMATION: PCR primer

<400> SEQUENCE: 10
cgagctccac cgcggtggcg gcccgtcgac cctgcaggca aaaaatctc                 49

<210> SEQ ID NO 11
<211> LENGTH: 31
<212> TYPE: DNA
<213> ORGANISM: Artificial Sequence
<220> FEATURE:
<223> OTHER INFORMATION: PCR primer

<400> SEQUENCE: 11
cgggatccaa aaagccttcc attttctatt t                                    31

<210> SEQ ID NO 12
<211> LENGTH: 29
<212> TYPE: DNA
<213> ORGANISM: Artificial Sequence
<220> FEATURE:
<223> OTHER INFORMATION: PCR primer

<400> SEQUENCE: 12
ttgcagccat ggtaaaatct tggtttatt                                       29

<210> SEQ ID NO 13
<211> LENGTH: 25
<212> TYPE: DNA
<213> ORGANISM: Artificial Sequence
<220> FEATURE:
<223> OTHER INFORMATION: PCR primer

<400> SEQUENCE: 13
tgaattccca tggctcgtga agcgg                                           25

<210> SEQ ID NO 14
<211> LENGTH: 37
<212> TYPE: DNA
<213> ORGANISM: Artificial Sequence
<220> FEATURE:
<223> OTHER INFORMATION: PCR primer

<400> SEQUENCE: 14
```

```
ggtgatgatg atccttgcca actaccttag tgatctc                              37

<210> SEQ ID NO 15
<211> LENGTH: 25
<212> TYPE: DNA
<213> ORGANISM: Artificial Sequence
<220> FEATURE:
<223> OTHER INFORMATION: PCR primer

<400> SEQUENCE: 15
tgaattccca tggctcgtga agcgg                                           25

<210> SEQ ID NO 16
<211> LENGTH: 38
<212> TYPE: DNA
<213> ORGANISM: Artificial Sequence
<220> FEATURE:
<223> OTHER INFORMATION: PCR primer

<400> SEQUENCE: 16
gctctagatt agtgatgatg gtgatgatga tccttgcc                             38

<210> SEQ ID NO 17
<211> LENGTH: 29
<212> TYPE: DNA
<213> ORGANISM: Artificial Sequence
<220> FEATURE:
<223> OTHER INFORMATION: PCR primer

<400> SEQUENCE: 17
gatggatcct tgctgttgca tcgaaagag                                       29

<210> SEQ ID NO 18
<211> LENGTH: 37
<212> TYPE: DNA
<213> ORGANISM: Artificial Sequence
<220> FEATURE:
<223> OTHER INFORMATION: PCR primer

<400> SEQUENCE: 18
cactggtacc cgggaattgt gacctctcgg gagaatc                              37

<210> SEQ ID NO 19
<211> LENGTH: 77
<212> TYPE: DNA
<213> ORGANISM: Artificial Sequence
<220> FEATURE:
<223> OTHER INFORMATION: ligation oligo

<400> SEQUENCE: 19
gatgtctaga agcaacgtaa aaaaacccgc cccggcgggt tttttatac ccgtagtatc      60 cccagcggcc gcggtac                                                    77

<210> SEQ ID NO 20
<211> LENGTH: 22
<212> TYPE: DNA
<213> ORGANISM: Artificial Sequence
<220> FEATURE:
<223> OTHER INFORMATION: PCR primer

<400> SEQUENCE: 20
cagactaata ccaatccaag cc                                              22

<210> SEQ ID NO 21
<211> LENGTH: 21
```

```
<212> TYPE: DNA
<213> ORGANISM: Artificial Sequence
<220> FEATURE:
<223> OTHER INFORMATION: PCR primer

<400> SEQUENCE: 21
ctatcagagg tagttggcgt c                                              21

<210> SEQ ID NO 22
<211> LENGTH: 21
<212> TYPE: DNA
<213> ORGANISM: Artificial Sequence
<220> FEATURE:
<223> OTHER INFORMATION: PCR primer

<400> SEQUENCE: 22
cactacattt cgctcatcgc c                                              21

<210> SEQ ID NO 23
<211> LENGTH: 20
<212> TYPE: DNA
<213> ORGANISM: Artificial Sequence
<220> FEATURE:
<223> OTHER INFORMATION: PCR primer

<400> SEQUENCE: 23
tattccgact tccccagagc                                                20

<210> SEQ ID NO 24
<211> LENGTH: 19
<212> TYPE: DNA
<213> ORGANISM: Artificial Sequence
<220> FEATURE:
<223> OTHER INFORMATION: PCR primer

<400> SEQUENCE: 24
catcaatacc tcggtctag                                                 19

<210> SEQ ID NO 25
<211> LENGTH: 19
<212> TYPE: DNA
<213> ORGANISM: Artificial Sequence
<220> FEATURE:
<223> OTHER INFORMATION: PCR primer

<400> SEQUENCE: 25
acacatagta tgcccggtc                                                 19

<210> SEQ ID NO 26
<211> LENGTH: 34
<212> TYPE: DNA
<213> ORGANISM: Artificial Sequence
<220> FEATURE:
<223> OTHER INFORMATION: PCR primer

<400> SEQUENCE: 26
tatagggccc agctataggt ttacattttt accc                                34

<210> SEQ ID NO 27
<211> LENGTH: 34
<212> TYPE: DNA
<213> ORGANISM: Artificial Sequence
<220> FEATURE:
<223> OTHER INFORMATION: PCR primer

<400> SEQUENCE: 27
```

-continued gtcctgcagt tatccatttg tagatggagc ttcg    34

<210> SEQ ID NO 28
<211> LENGTH: 125
<212> TYPE: DNA
<213> ORGANISM: Artificial Sequence
<220> FEATURE:
<223> OTHER INFORMATION: modified multi cloning site

<400> SEQUENCE: 28
gaattcgggc cgtcgaccc tgcaggcccg gggatccata tgccatggtc tagatgatca    60
tcatcaccat catcactaat ctagagagct cctcgaggcg gccgcggtac catgcatgca    120
agctt    125

<210> SEQ ID NO 29
<211> LENGTH: 97
<212> TYPE: DNA
<213> ORGANISM: Artificial Sequence
<220> FEATURE:
<223> OTHER INFORMATION: synthetic sequence

<400> SEQUENCE: 29
ctgcaggatc ctatagggag accacaacgg tttccctcta gtaataattt tgtttaactt    60
taagaaggag atatacatat ggctagcatt tccatgg    97

<210> SEQ ID NO 30
<211> LENGTH: 24
<212> TYPE: DNA
<213> ORGANISM: Artificial Sequence
<220> FEATURE:
<223> OTHER INFORMATION: PCR primer

<400> SEQUENCE: 30
catgccatgg tccgtcctgt agaa    24

<210> SEQ ID NO 31
<211> LENGTH: 34
<212> TYPE: DNA
<213> ORGANISM: Artificial Sequence
<220> FEATURE:
<223> OTHER INFORMATION: PCR primer

<400> SEQUENCE: 31
gccaagcttg tacagttctt tcggcttgtt gccc    34

<210> SEQ ID NO 32
<211> LENGTH: 24
<212> TYPE: DNA
<213> ORGANISM: Artificial Sequence
<220> FEATURE:
<223> OTHER INFORMATION: PCR primer

<400> SEQUENCE: 32
catgccatgg tccgtcctgt agaa    24

<210> SEQ ID NO 33
<211> LENGTH: 32
<212> TYPE: DNA
<213> ORGANISM: Artificial Sequence
<220> FEATURE:
<223> OTHER INFORMATION: PCR primer

<400> SEQUENCE: 33
ctgggtacct tattgtttgc ctccctgctg cg    32

```
<210> SEQ ID NO 34
<211> LENGTH: 27
<212> TYPE: DNA
<213> ORGANISM: Artificial Sequence
<220> FEATURE:
<223> OTHER INFORMATION: PCR primer

<400> SEQUENCE: 34
ggatccatgc gtgaagcggt tatcgcc                                              27

<210> SEQ ID NO 35
<211> LENGTH: 37
<212> TYPE: DNA
<213> ORGANISM: Artificial Sequence
<220> FEATURE:
<223> OTHER INFORMATION: PCR primer

<400> SEQUENCE: 35
ggtgatgatg atccttgcca actaccttag tgatctc                                   37

<210> SEQ ID NO 36
<211> LENGTH: 37
<212> TYPE: DNA
<213> ORGANISM: Artificial Sequence
<220> FEATURE:
<223> OTHER INFORMATION: PCR primer

<400> SEQUENCE: 36
ggggtaccag ttgtagggag ggatccatgc gtgaagc                                   37

<210> SEQ ID NO 37
<211> LENGTH: 38
<212> TYPE: DNA
<213> ORGANISM: Artificial Sequence
<220> FEATURE:
<223> OTHER INFORMATION: PCR primer

<400> SEQUENCE: 37
gctctagatt agtgatgatg gtgatgatga tccttgcc                                  38

<210> SEQ ID NO 38
<211> LENGTH: 38
<212> TYPE: DNA
<213> ORGANISM: Artificial Sequence
<220> FEATURE:
<223> OTHER INFORMATION: PCR primer

<400> SEQUENCE: 38
ctaatctaga gagctcgtct ataggaggtt ttgaaaag                                  38

<210> SEQ ID NO 39
<211> LENGTH: 21
<212> TYPE: DNA
<213> ORGANISM: Artificial Sequence
<220> FEATURE:
<223> OTHER INFORMATION: PCR primer

<400> SEQUENCE: 39
ccagaaagaa gtatgctttg g                                                    21
```

PLASTID TRANSFORMATION USING MODULAR VECTORS

CROSS-REFERENCE TO RELATED APPLICATIONS

Figure 1:
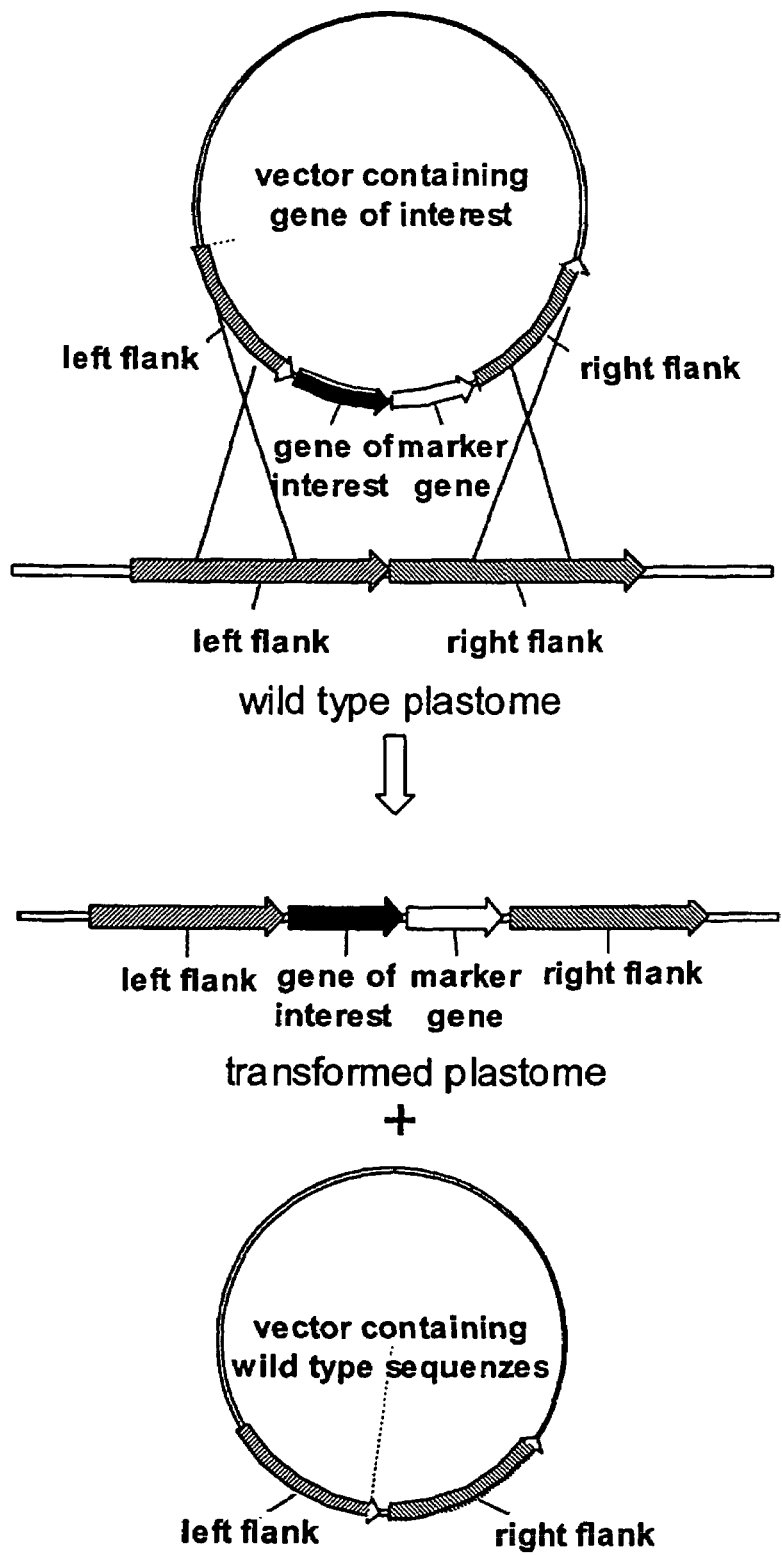

This application is the U.S. National Stage of International Application PCT/EP2003/008549, filed Aug. 1, 2003, which published in English on Feb. 19, 2004 and designates the U.S., and which claims the benefit of German Patent Application No. 102 36 011.4 filed Aug. 6, 2002; both of which are hereby incorporated herein in their entirety by reference.

FIELD OF INVENTION FIELD OF INVENTION

The present invention relates to plant biotechnology in general and more particularly to a process and vectors for plastid transformation of plants. Specifically, the present invention provides a process of genetic transformation of plant plastids, vectors for the process, and plants or plant cells obtained or obtainable according to the process of the invention.

BACKGROUND OF THE INVENTION

According to generally accepted knowledge, two classes of cell organelles, i.e. plastids and mitochondria, are derived from initially independent prokaryotes that were taken up into a predecessor of present day eukaryotic cells by separate endosymbiotic events (Gray, 1991). As a consequence, these organelles contain their own DNA, DNA transcripts in the form of messenger RNA, ribosomes, and at least some of the necessary tRNAs that are required for decoding of genetic information (Marechal-Drouard et al., 1991).

While, shortly after endosymbiotic uptake, these organelles were genetically autonomous since they contained all the elements necessary to drive prokaryotic life, this autonomy was reduced during evolution by transfer of genetic information to the cell's nucleus. Nevertheless, their genetic information is of sufficient complexity to make recent cell organelles an attractive target for gene technology. This is particularly the case with plastids, because these organelles still encode about 50% of the proteins required for their main function inside the plant cell, photosynthesis. Plastids also encode their ribosomal RNAs, the majority of their tRNAs and ribosomal proteins. In total, the number of genes in the plastome is in the range of 120 (Palmer, 1991). The vast majority of proteins that are found in plastids are, however, imported from the nuclear/cytosolic genetic compartment.

Plastids Can Be Genetically Transformed

With the development of general molecular cloning technologies, it became soon possible to genetically modify higher plants by transformation. The main emphasis in plant transformation was and still is on nuclear transformation, since the majority of genes, ca. 26,000 in the case of *Arabidopsis thaliana*, the complete sequence of which was recently published (The Arabidopsis Genome Initiative, 2000), is found in the cell's nucleus. Nuclear transformation was easier to achieve, since biological vectors such as *Agrobacterium tumefaciens* were available, which could be modified to efficiently enable nuclear transformation (Galvin, 1998). In addition, the nucleus is more directly accessible to foreign nucleic acids, while the organelles are surrounded by two envelope membranes that are, generally speaking, not permeable to macromolecules such as DNA.

A capability of transforming plastids is highly desirable since it could make use of the high gene dosage in these organelles that bears the potential of extremely high expression levels of transgenes. In addition, plastid transformation is attractive because plastid-encoded traits are not pollen transmissible; hence, potential risks of inadvertent transgene escape to wild relatives of transgenic plants are largely reduced. Other potential advantages of plastid transformation include the feasibility of simultaneous expression of multiple genes as a polycistronic unit and the elimination of positional effects and gene silencing that may result following nuclear transformation.

Methods that allow stable transformation of plastids could indeed be developed for higher plants. To date, two different methods are available, i.e. particle bombardment of tissues, in particular leaf tissues (Svab et al., 1990), and treatment of protoplasts with polyethylene glycol (PEG) in the presence of suitable transformation vectors (Koop et al., 1996). Both methods mediate the transfer of plasmid DNA across the two envelope membranes into the organelle's stroma.

Conventional methods for plastid transformation usually rely on the selection for the insertion of an antibiotic resistance marker cassette into the plastome such as an expression cassette containing the gene aadA (encoding the enzyme aminoglycoside adenyl transferase), which confers resistance to inhibitors like Spectinomycin or Streptomycin (U.S. Pat. No. 5,877,402) or aphA-6 (encoding the enzyme aminoglycoside phosphotransferase A-6) which confers resistance to kanamycin (Huang et. al., 2002). Alternatively, selection is achieved by replacing a complete resident plastid gene by a mutant gene which confers resistance to selection inhibitors (U.S. Pat. No. 5,451,513). These selection marker genes that are needed for the selection of transgenic plant cells from a vast background of untransformed cells code for antibiotic or herbicide resistance. The selection marker gene or the mutant plastid gene is included in the integrating region, which is flanked by homologous regions directing the plastome integration. Selection for plastid transformants is then achieved by cultivating transformed plant material on medium containing the appropriate inhibitor. As these marker genes are stably integrated into the genome together with the genes of interest, they will remain in the homoplastomic transgenic plants although they are not required for the function of the genes of interest. These remaining marker genes are a main issue of criticism of plant biotechnology. Construction of a selection system which does not result in a resistance gene in the transgenic plant is, therefore, highly desirable (lamtham and Day, 2000).

Conventional plastid transformation technology is described in Heifetz, 2000 and Koop et al., 1996.

Plastid transformation vectors usually contain one or more gene(s) of interest flanked by two regions of the insertion site, which are necessary for the stable introduction of the engineered sequences into the plastome by homologous recombination events (U.S. Pat. Nos. 5,877,402, 5,451,513). However, substantial cloning work is needed to generate the transformation vector molecules which contain a large number of different fragments: two flanks, a marker gene, one or more gene(s) of interest and regulatory elements such as promoter, 5'-UTR, 3'-UTR or spacer elements.

The cloning of transformation vectors is problematic in cases wherein (at least one of) the cloned gene(s) has a toxic effect on the bacteria used for cloning. Moreover, using the highly desirable potential to co-express a series of introduced transgenes is limited by the overall size of the transforming plasmid.

One major complication in achieving plastid transformation is the high copy number of the plastome. Following transfer of the vector DNA into the plastids only one or very few copies of the introduced molecules will recombine with the plastome. Thus initially only a small proportion of recombinant plastome molecules are generated in the background of a vast majority of wild type plastome molecules ("heteroplastomic status"). By a very time consuming process of segregation under selective pressure it is possible to eliminate the original wild type copies of the plastome and achieve a "homoplastomic recombinant status" being characterized by the sole presence of recombinant plastome molecules. Achieving the homoplastomic status is supported by several cycles of regeneration on selective medium containing the appropriate antibiotics. Usually 3-5 of such cycles are necessary to obtain the homoplastomic recombinant status. The presence of remaining copies of wild type plastome can be monitored by molecular analysis like PCR or Southern Hybridization. As several weeks are needed for one regeneration cycle it takes several months to generate hormoplastomic plastid transformants.

Therefore, it is an object of the invention to provide a novel, efficient, rapid and highly versatile process of genetic transformation of plant plastids, whereby genetically stable transgenic plants or plant cells may be produced.

It is another object of the invention to provide a process of genetic transformation of plant plastids, which allows a significant reduction of the number of regenerations cycles needed to achieve homoplastomic plants.

It is another object of the invention to provide a process of genetic transformation of plant plastids, which allows expression of multiple genes of interest (polycistronic expression).

It is a further object to provide vectors which can be used in a modular fashion, thus reducing the cloning work and the overall size of the plasmid molecules.

It is a further object to provide vectors which allow the cloning of sequences having toxic effects on the bacteria used for cloning.

It is a further object to provide a method that allows the generation of transformants which do not carry a resistance marker gene in the final plant or plant cell.

GENERAL DESCRIPTION OF THE INVENTION

The above objects are achieved by a process of generating transgenic plants or plant cells transformed on their plastome, comprising
(a) introducing into plant plastids a first DNA molecule and a second DNA molecule, wherein said first DNA molecule contains a first region homologous to a region of the plastome for directing plastome integration and a first sequence of interest, and said second DNA molecule contains a second region homologous to a region of the plastome for directing plastome integration and a second sequence of interest, whereby a sequence segment of said first sequence of interest is homologous to a sequence segment of said second sequence of interest,
(b) selecting transformants having an integration sequence stably integrated in the plastome, whereby said integration sequence contains at least a portion of said first and at least a portion of said second sequence of interest as a continuous sequence.

Preferred embodiments are defined by the subclaims.

It has been surprisingly found that it is possible to generate transgenic plants or plant cells transformed on their plastomes by introducing into plant plastids at least two DNA molecules containing overlapping sequences, which results in a continuous integration sequence in the final transplastomic plant. The process of the invention features several important advantages over conventional plastid transformation processes. These advantages are given below.

The process of the invention comprises introducing a first and a second DNA molecule into plastids of a plant to be transformed. These DNA molecules which are used as vectors may be introduced consecutively, i.e. in two separated steps, or simultaneously, i.e. in a one-step procedure. It is less laborious and therefore preferred to introduce said two DNA molecules in a one-step procedure, e.g. by using a mixture of said DNA molecules. For introducing said DNA molecules, known transformation methods may be used (see below).

The design of said two DNA molecules is of central importance for the process of the invention. Said first DNA molecule contains a first region homologous to a region of the plastome for directing plastome integration and a first sequence of interest. Said second DNA molecule contains a second region homologous to a region of the plastome for directing plastome integration and a second sequence of interest. Thus, one region homologous to a region of the plastome is sufficient for each DNA molecule. Preferably, said first or said second DNA molecule contains only one region homologous to a region of the plastome for directing plastome integration. More preferably, said first and said second DNA molecule both contain only one region homologous to a region of the plastome for directing plastome integration.

Said homologous regions direct integration of each DNA molecule to a desired site of the plastome. The first and the second homologous region together determine the type of DNA modification (e.g. insertion, deletion) of the plastome by the process of the invention. In a preferred embodiment, the aim of performing the process of the invention is to introduce an integration sequence into the plastome without any further plastome modification like a deletion of plastome sequences. Preferably, said homologous regions of the first and the second DNA molecules correspond together to a continuous plastome sequence. Generally, said homologous regions are derived from plastomes of the plant species to be transformed. As long as sufficient homology for homologous recombination is guaranteed, the homologous regions may be derived from other plant species, preferably however, from closely related plant species.

The length of each homologous region for plastome integration may vary in a wide range as long as the recombination frequency is sufficient. Each homologous region may have a length of between 100 and 5000 bp. Usually, the recombination frequency decreases as the length of the homologous regions decreases. Therefore the length is preferably at least 200 to 300 bp. More preferably, the length is between 500 and 2000 bp, most preferably between 500 and 1000 bp.

Said sequences of interest may contain any nucleotide sequence to be integrated into the plastome. As a typical example, said sequences of interest contain a gene to be expressed. Said first and said second sequence of interest may each contain a fragment of a gene to be expressed, whereby said gene is assembled in said integration sequence. The invention is highly versatile in this respect. Preferably, however, said first and said second sequence of interest are different.

Said first sequence of interest contains a sequence segment that is homologous to a sequence segment of said second sequence of interest. Thus, this homologous segment is an overlapping region of said first and said second sequence of interest. The homologous sequence segment allows recombination of said first and said second sequence of interest such that an integration sequence is formed in the plastome, whereby said integration sequence contains at least a portion of said first and at least a portion of said second sequence of interest as a continuous sequence (cf. FIG. 5). The sequence segment in a sequence of interest is preferably positioned at the distal end of the sequence of interest with respect to said homologous region that directs plastome integration.

As a minimum requirement, said first and said second sequence of interest each contains said homologous sequence segment, i.e. a sequence that is of sufficient homology to enable homologous recombination between said first and said second sequence of interest. Preferably, the homologous sequence segment of the first and of the second sequence of interest are identical.

Said sequence segment may be or may contain a sequence (or a part thereof) involved in expression of an RNA and/or a protein. Said sequence segment may be or may contain a sequence involved in regulating transcription or translation of a coding sequence (e.g. a promoter, a 5' or a 3' untranslated sequence, a ribosome binding site etc. or parts thereof. Further, said sequence segment may be or may contain a coding sequence (or a part thereof) of a protein to be expressed. In the aforementioned cases, the sequence segment of said first sequence of interest and the sequence segment of said second sequence of interest are preferably identical in order not to perturb the function of said regulating or said coding sequence. Alternatively, said sequence segment may have the sole purpose of allowing recombination between said first and said second sequence of interest for forming said integration sequence and may not be involved in expression of an RNA or protein.

Figure 6:
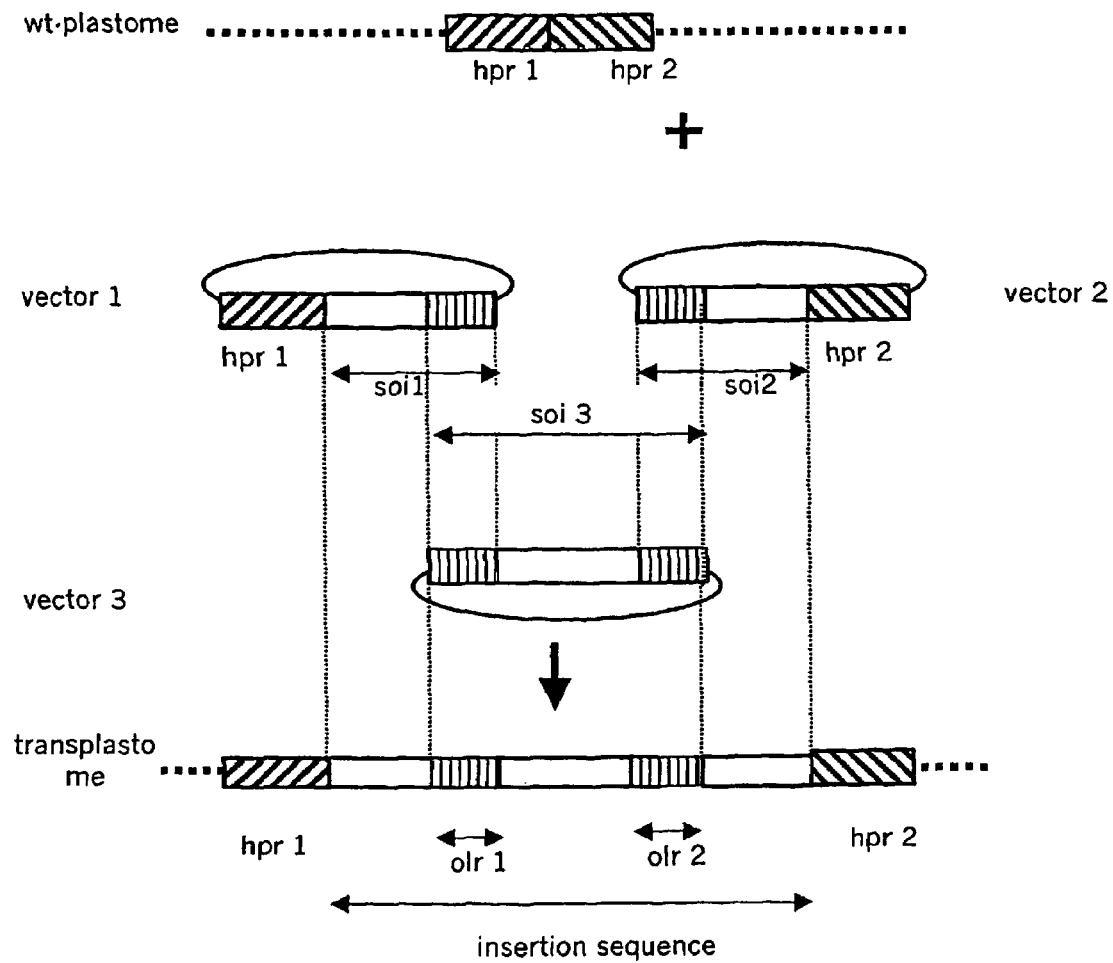

Said sequence segment(s) are typically part of the transplastome of the transgenic plant or plant cells generated according to the invention (cf. FIG. 6 and 6). Said sequence segment may be part of a transcription unit, whereby it may become part of a transcript formed from said transcription unit. If said sequence segment (or a part thereof) is undesired in such a transcript (e.g. if said sequence segment interrupts a coding sequence that codes for a protein to be expressed), the undesired part may be cut out by RNA splicing. In this case, an intron, notably a self-splicing intron like a group I or a group II intron, may be included in said sequence segment for splicing out undesired parts. Self-splicing introns from many sources and their use in genetic engineering are known in the art. The first sequence of interest may provide a 5' part of the intron and the second sequence of interest may provide a 3' part of the intron, whereby a functional intron may be assembled when said integration sequence in formed.

Said first and said second sequence of interest may be identical, leading to an integration sequence consisting of said sequence of interest. In this limiting case, each sequence of interest may be considered to consist of said homolgous sequence segment. This limiting case is not a preferred case of the invention. Preferably, said first or said second sequence of interest contains a sequence in addition to said homologous sequence segment. More preferably, said first and said second sequence of interest each contains a sequence in addition to said homologous sequence segment, whereby said additional sequences in said first and said second sequence of interest are different.

Recombination between said overlapping regions (homologous sequence segments) of the vectors can take place inside the plastome to form said integration sequence. Said integration sequence preferably comprises sequence portions from said first and from said second sequence of interest. If said first and said second sequence of interest each contains a gene of interest, an integration sequence may be formed comprising two genes of interest. Thus, the process of the invention may be used for assembling a desired integration sequence from said first and said second sequence of interest. The assembly of the integration sequence may be used to generate in the plastids a new function not present in one of said sequences of interest alone. As an example, a gene of interest consisting of a coding sequence and of various regulatory sequences may be assembled to a functional form in said integration sequence. Further, a coding sequence of interest in said first sequence of interest may be combined with a promoter or other regulatory sequences provided with said second sequence of interest (or vice versa). In this way, a regulatory sequence giving rise to a desired expression of said coding sequence may be selected or screened for.

Further, a coding sequence for expressing a protein of interest may be assembled in said integration sequence, whereby said first and said second sequence of interest (and optionally further sequences of interest from further vectors) each provide a part of said coding sequence to said integration sequence. Self-splicing introns may be used for achieving the correct reading frame of the protein to be expressed on messenger RNA level.

The process of the invention may comprise introducing one or more additional DNA molecules into said plant plastids in addition to said first and said second DNA molecule. Said additional DNA molecule(s) comprise(s) additional sequence(s) of interest. If a third DNA molecule is introduced, said third DNA molecule preferably contains a sequence segment homologous to a sequence segment of said first sequence of interest and a sequence segment homologous to said second sequence of interest Said third DNA molecule does preferably not have a homologous region for plastome integration.

After transformation, transformants are selected that contain the desired integration sequence. Selection is typically supported by an inhibitor or antibiotic the transformants are resistant against due to a marker gene. Selection may further comprise allowing segregation of transformed and untransformed sectors (e.g. on leaves). Transformants or transformed sectors may be identified by molecular analysis, e.g. PCR and Southern blotting. Further, transformants or transformed sectors may be identified phenotypically, e.g. by the expression of a transgene. A transgene may e.g. be detected by Western blotting, by a characteristic enzymatic activity or by another characteristic property like optical, notably fluorescent property.

A marker gene for selecting transformants may be introduced into a plastome with said first or said second sequence of interest.

As noted above, said first second sequence of interest may provide a fragment of a marker gene to said integration sequence and said second sequence of interest may provide another fragment of said marker gene, whereby said fragments are combined to a functional marker gene in said integration sequence. Preferably, said first sequence of interest contains a 5' part of a marker gene and said second sequence of interest contains a 3' part of said marker gene. Said integration sequence may then contain said marker gene such that it can be expressed. This embodiment allows selection for integration of both vectors and recombination to form said integration sequence.

Selectable marker-free transgenic plants or plant cells may be obtained in the process of the invention by designing said first and said second sequence of interest of said first and said second DNA molecule, respectively, such that the selectable marker gene in the integration sequence is flanked by sequence elements homologous to each other for allowing excision of the marker gene by homologous recombination similarly as described by Iamtham and Day (Nature Biotechnol. (2000) 18, 1172-1176). In this embodiment, said first sequence of interest may contain upstream of a 5' part of said marker gene a sequence element homologous to a sequence element located downstream of a 3' part of said marker gene on the second sequence of interest, whereby said sequence elements enable excision by homologous recombination of a part of said integration sequence that comprises said 5' and/or said 3' part of said marker gene. Excision of the marker gene typically requires release of selection pressure said marker gene provides resistance against.

Said first and said second sequence of interest may each contain a complete marker gene. Preferably, however, said first sequence of interest may contain said 5' part of said marker gene and said second sequence of interest may contain said 3' part of said marker gene, whereby neither said 5' part nor said 3' part is capable of conferring resistance in the absence of said 3' part or said 5' part, respectively. As an example, said 5' part may be: a promoter, 5'-untranslated sequences, and the coding sequence of said marker gene. Said 3' part may be: the coding sequence of said marker gene, and 3'-untranslated sequences.

The invention provides a further embodiment that allows to produce marker free transplastomic plants. This may be achieved by including a selectable marker gene in one of said DNA molecules outside of a sequence unit consisting of said region homologous to a region of the plastome and said sequence of interest. Such a positioning of a marker gene allows loss of said marker gene in the course of recombination events that take place. A selectable marker gene may be included in said first or said second DNA molecule in the described fashion, or in said first and said second DNA molecule. If a selectable marker gene is included in said first and in said second DNA molecule, these selectable marker genes may be the same or they may be different selectable marker genes. The positioning of said marker gene outside of said sequence unit results in excision of the marker gene out of the plastome in the course of recombination events envisaged in this invention, making amenable marker free transplastomic plants. It is obvious to the skilled person, that the inhibitor or antibiotic for the used marker gene is applied only transiently in the selection of step (b). At a later stage, the antibiotic is left out from the medium in order to allow loss of the marker gene(s) by homologous recombination events mediated by duplicated sequences, which have been generated during vector integration In a specific embodiment of the process of producing marker free transplastomic plants, a selectable marker gene is split into a first and a second fragment, whereby said first fragment is incorporated in said first DNA molecule outside of a first sequence unit and said second fragment is incorporated in said second DNA molecule outside of a second sequence unit. Said first sequence unit consists of said first homologous region and said first sequence of interest. Said second sequence unit consists of said second homologous region and said second sequence of interest.

The process of the invention may be applied to all plants. Preferably, it is applied to multi-cellular plants. Most preferably, the process of the invention is applied to crop plants. Examples of crop plants are given in the definitions.

The invention further provides a kit-of-parts comprising a first and a second DNA molecule as defined herein. The invention further provides a DNA molecule for plastid transformation containing one region homologous to a region of a plastome for directing plastome integration and a sequence of interest. Further, a library of DNA molecules as defined herein is provided, whereby each of said DNA molecules contains a different sequence of interest. Such a library may be created by cloning a mixture of DNA sequences of interest into a vector that contains a region homologous to a region of a plastome for directing plastome integration. The library may be maintained by transforming the DNA molecules into cells like bacterial (e.g. E. coli) or plant cells. Also, plants or plant cells transformed with said DNA molecules of said kit-of-parts or with said DNA molecule of the invention is provided. The invention also relates to plant cells and plants obtained or obtainable by the process of the invention.

Advantages of the Process of the Invention

The process described herein may be applied to introduce sequences of interest such as genes or regulatory elements or to introduce mutations such as point mutations insertions or deletions into the plastome.

The process of the invention allows to generate transplastomic plants, whereby the homoplastomic state can be attained after less regeneration cycles than with prior art processes. Depending on the particular embodiment, homoplastomic plants may be achieved after 0 to 4 regeneration cycles, preferably after 2 cycles, and more preferably after 1 regeneration cycle. In special embodiments, the homoplastomic state is achieved in primary transformants without a regeneration cycle. Thus, the process of the invention allows an enormous reduction of the time required to achieve homoplastomic transplastomic plants. The reasons for this surprising efficiency improvement is presently unclear. Compared to conventional plastid transformation, the method described herein is faster, because fewer steps are necessary to obtain homoplastomic plants.

The method allows the use of smaller transformation vectors for which cloning is simpler than in the case of conventional plastid transformation vectors.

The method relieves plastid transformation from any limitation on the number or size of sequences to be introduced, because an unlimited number of transformation vectors with overlapping sequences may be used.

The method relieves plastid transformation from any limitation imposed by sequences, which are toxic for the bacteria used for cloning, because the toxic sequences may be cloned into two different vector molecules in a way that each of them separately can not be toxic, even if they are expressed into a protein sequence.

Moreover the method described herein allows the use of combinatorial vector libraries, whereby the vectors of the library contain different sequences of interest.

The method can be applied to generate transformants, whereby the final plant does not carry any resistance marker gene.

Any of the above mentioned aspects of this new method offers substantial advantage compared to conventional plastid transformation. Taken together the process and vectors of this invention constitute an enormous progress on both speed, usability and flexibility of plastid transformation in general.

DEFINITIONS

3'-UTR: transcribed but not translated region of a (->) gene, downstream of a (->) coding region;

5'-UTR: transcribed but not translated region of a (->) gene, upstream of a (->) coding region; in (->) plastid (->) genes, the 5'-UTR contains sequence information for translation initiation (ribosome binding site, (->) RBS) close to its 3' end;

aadA: (->) coding region of bacterial aminoglycoside adenyl transferase, a frequently used protein, that detoxifies antibiotic (->) selection inhibitors spectinomycin and/or streptomycin;

aphA-6 (->) coding region of bacterial aminoglycoside phosphotransferase A6, a protein that detoxifies the antibiotic (->) selection inhibitor: kanamycin chloroplast: (->) plastid containing chlorophyll;

coding region: nucleotide sequence containing the information for a) the amino acid sequence of a polypeptide or b) the nucleotides of a functional RNA; coding regions are optionally interrupted by one or more (->) intron(s);

flank, flanking region: DNA sequences at the 5' and 3' ends of inserts in a conventional (->) plastid (->) transformation (->) vector, which mediate integration into the target (->) plastome of sequences between the flanks by double reciprocal (->) homologous recombination. By the same mechanism, sequences can be modified or removed from the target (->) plastome. Thus, the flanks of the (->) plastid (->) transformation (->) vector determine, where changes in the target (->) plastome are generated by (->) transformation;

gene expression: process turning sequence information into function; in (->) genes encoding polypeptides, gene expression requires the activity of a (->) promoter, which initiates and directs RNA polymerase activity, leading to the formation of a messenger RNA, which is subsequently translated into a polypeptide; in (->) genes encoding RNA, the (->) promoter-mediated activity of RNA polymerase generates the encoded RNA;

gene(s): nucleotide sequence(s) encoding all elements, which are required to secure function e.g. expression independently; genes are organised in (->) operons, which contain at least one complete (->) coding region; in (->) genes encoding polypeptides, these elements are: (1) a (->) promoter, (2) a 5' untranslated region ((->) 5'-UTR), (3) a complete (->) coding region, (4) a 3' untranslated region ((->) 3'-UTR); in (->) genes encoding RNA, the (->) 5'-UTR and the (->) 3'-UTR are missing; in (->) operons consisting of more than one (->) coding region, two subsequent complete (->) coding regions are separated by a (->) spacer, and (->) promoter, (->) 5'-UTR, and (->) 3'-UTR elements are shared by the (->)coding regions of that (->) operon; a fragment of a gene fully or partly misses at least one of the above-listed elements of a gene.

gene of interest: modified or newly introduced sequence: the purpose of a (->) transformation attempt;

genome: Complete DNA sequence of a cell's nucleus or a cell organelle;

GFP green fluorescent protein homologous recombination: process leading to exchange, insertion or deletion of sequences due to the presence of one or more (->) flanks with sufficient sequence homology to a target site in a (->) genome;

intron: sequence interrupting a (->) coding region;

operon: organisational structure of several (->) genes sharing a promoter;

plant(s): organism(s) that contain(s) (->) plastids in its (their) cells; this invention particularly relates to multicellular (->) plants; these include the group of gymnosperms (such as pine, spruce and fir etc.) and angiosperms (such as the *monocotyledonous* crops maize, wheat, barley, rice, rye, Triticale, sorghum, sugar cane, *asparagus*, garlic, palm tress etc., and non-crop monocots, and the *dicotyledonous* crops tobacco, potato, tomato, rape seed, sugar beet, squash, cucumber, melon, pepper, Citrus species, egg plant, grapes, sunflower, soybean, alfalfa, cotton etc.), and no-crop dicots as well as ferns, liverworths, mosses, and multicellular green, red and brown algae;

plastid(s): organelle(s) with their own genetic machinery in (->) plant cells, occurring in various functionally and morphologically different forms, e.g. amyloplasts, (->) chloroplasts, chromoplasts, etioplasts, gerontoplasts, leukoplasts, proplastids etc;

plastome: complete DNA sequence of the (->) plastid;

promoter: nucleotide sequence functional in initiating and regulating transcription;

RBS, ribosomal binding site: DNA sequence element upstream of the (->) translation start codon of a (->) coding region, that mediates ribosome binding and translation initiation from the respective RNA transcript; RBS elements are either part of (->) 5'-UTRs or of (->) spacers;

selection inhibitor: chemical compound, that reduces growth and development of non-transformed cells or organelles stronger than that of transformed ones;

sequence of interest modified or newly introduced sequence of any length: the purpose of a (->) transformation attempt; if introduction of a sequence is not intended, the length of the sequence of interest can be zero, i.e. it can be of interest not to have a sequence of interest. In the present invention, a sequence of interest of a DNA molecule used as a vector has at least one sequence segment homologous to a sequence segment of another DNA molecule used as a vector.

transformation vector: cloned DNA molecule that was generated to mediate (->) transformation of a (->) genome;

transformation: process leading to the introduction, the excision or the modification of DNA sequences by treatment of (->) plants or plant cells including the use of at least one (->) transformation vector;

transgene: DNA sequence derived from one (->) genome, introduced into another one;

uidA: (i>) coding region of bacterial β glucuronidase, a frequently used reporter protein.

SHORT DESCRIPTION OF THE FIGURES

FIG. 1 Simplified scheme of recombination events in conventional plastid transformation: The integration of transformation vector sequences into the plastome takes place by two homologous recombination events mediated by two homologous flanks. The corresponding wild type region from the plastome is transferred to the plasmid vector.

Figure 2:
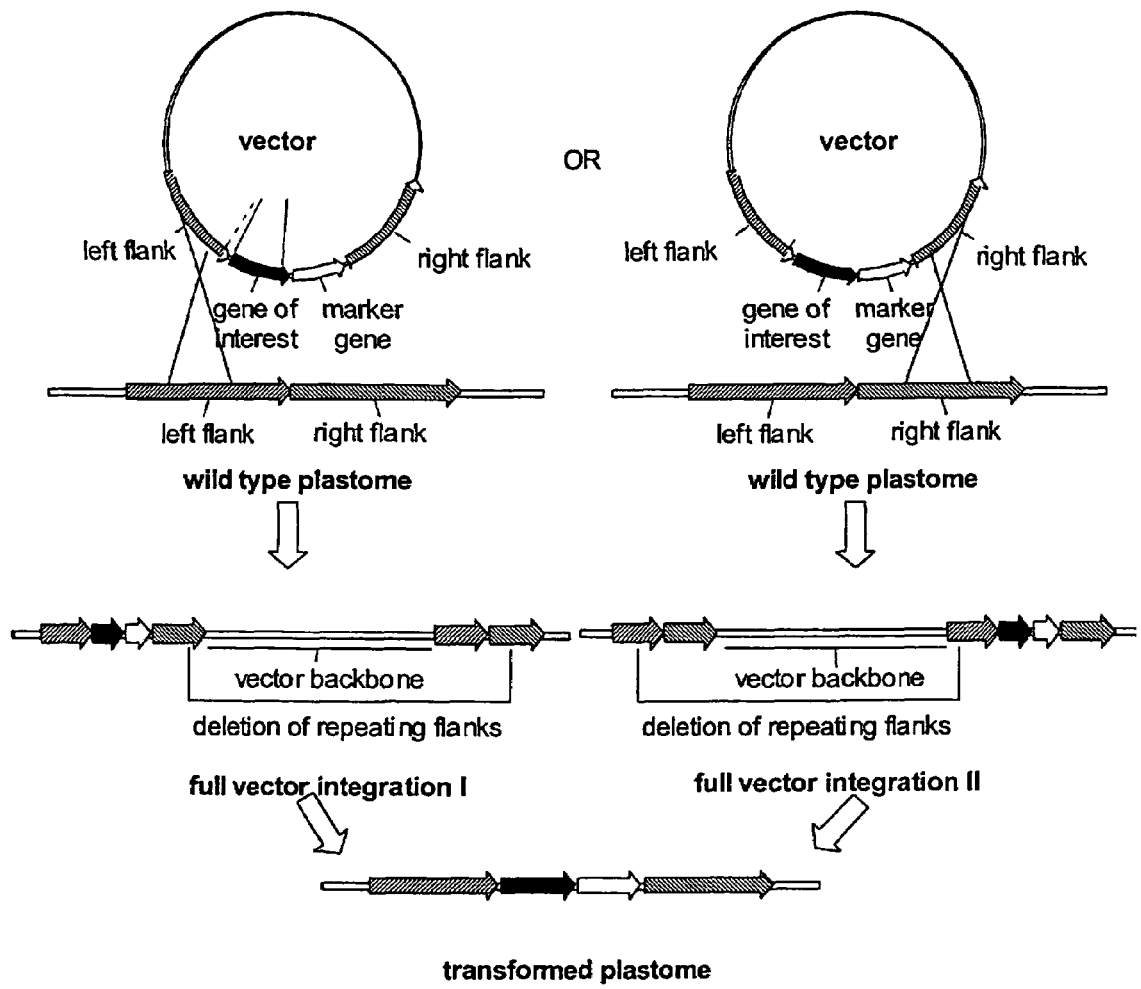

FIG. 2 Suggested model of recombination events in conventional plastid transformation based on our observations: the first homologous recombination via the left or the right flank leads to the transient (reversible) insertion of the whole transformation vector generating a duplication of the respective flanking sequence. A second homologous recombination via the right or the left flank, respectively, leads to the excision of the duplicated sequences. The corresponding wild type region from the plastome is transferred to the plasmid vector.

Figure 3:
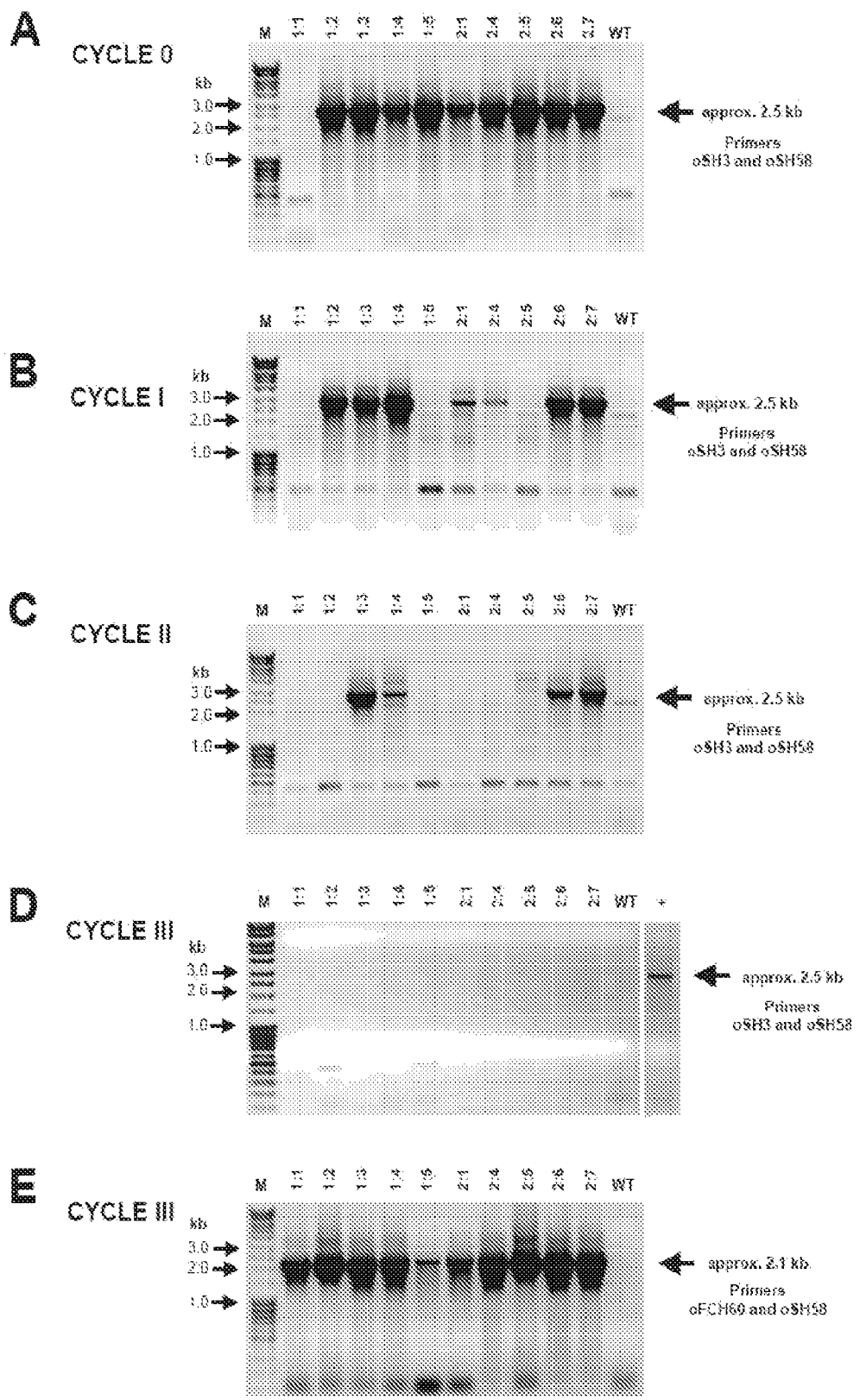

FIG. 3 PCR analysis of tobacco transformants transformed with pKCZ after up to three regeneration cycles (reference example). Gel A (cycle 0), Gel B (cycle I), Gel C (cycle II) and Gel D (cycle III) show the products obtained using primers oSH3 and oSH58 which are specific for detecting complete pKCZ integration. Gel E, illustrates that with the primer combination oFCH60 and oSH58 all the cycle-III lines still contain the aadA selection cassette even though not all carry complete vector insertion events (cf. example 1).

Figure 4:
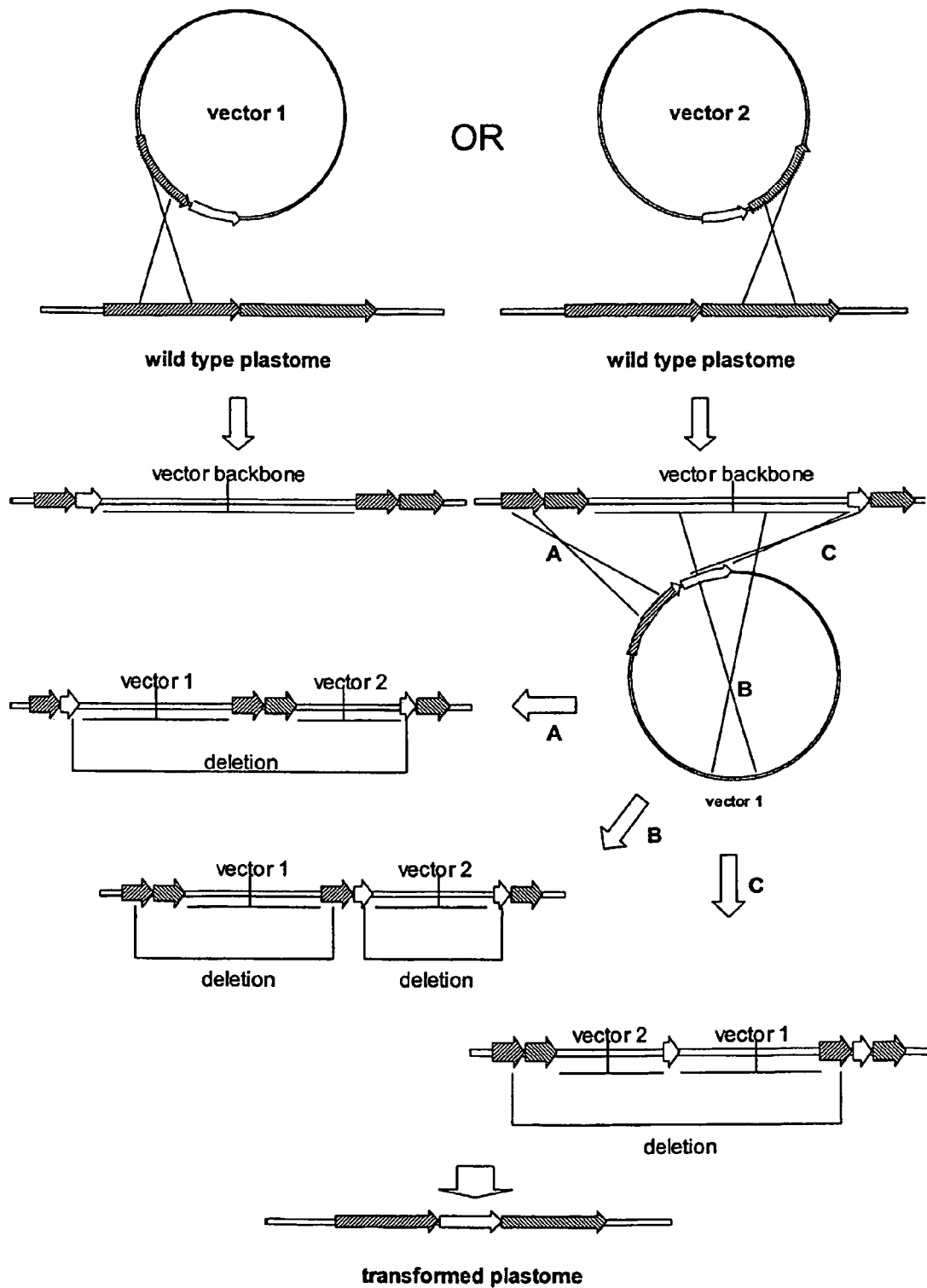

FIG. 4 Suggested model of recombination events by using modular vectors according to the invention (vector 1 and vector 2). The first integration step is shown for either vector 1 or vector 2. The following second integration step is shown only for vector 1 (on the right) into a plastome region already containing vector 2. The second integration step of vector 2 into a plastome region already containing vector 1 (not shown) proceeds in an analogous fashion. After full vector integration of both vectors, the final transformed plastome (bottom) is obtained by deletion events of homologous repetitive elements.

Figure 5:
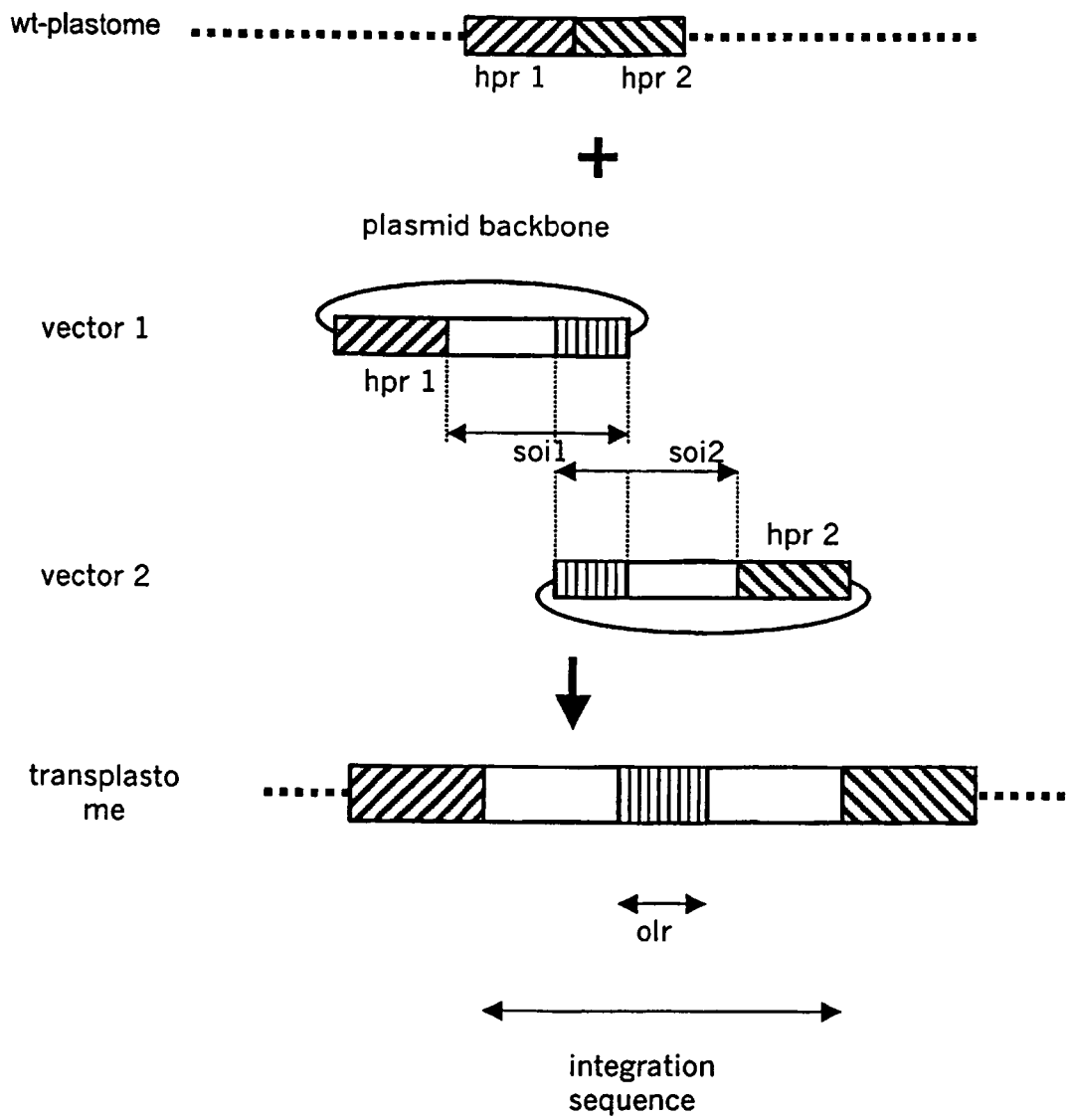

FIG. 5 Scheme showing the homologous region of vector 1 (hpr 1) and of vector 2 (hpr 2) for directing plastome integration by homologous recombination. hpr stands for homolgous plastome region. Further, the sequence of interest in both vectors is shown (white boxes plus vertically hatched box). The vertically hatched boxes (designated olr for overlapping region) represents a sequence segment of said first sequence of interest (soi) that is homologous to a sequence segment of said second sequence of interest (soi). These homologous sequence segments or overlapping regions allow recombination of vector 2 and vector 1 in the plastome. Within the sequences of interest, the homologous sequence segments are preferably positioned distal to the hpr sequences. At the bottom, the obtained transplastome containing the integration sequence is shown.

FIG. 6 Scheme showing the use of a further vector (vector 3) in addition to said fist and said second vector of the invention. Vector 3 does not have to contain a homologous region for plastome integration. Vector 3 has two homologous segments or overlapping regions (vertically hatched boxes). One overlapping region (olr1) shares homology with a homologous sequence segment of vector 1. The other overlapping region (olr2) shares homology with a homologous sequence segment of vector 2. olr1 and olr2 are preferably non identical. hpr, homologous plastome region; soi, sequence of interest; olr, overlapping region.

Figure 7:
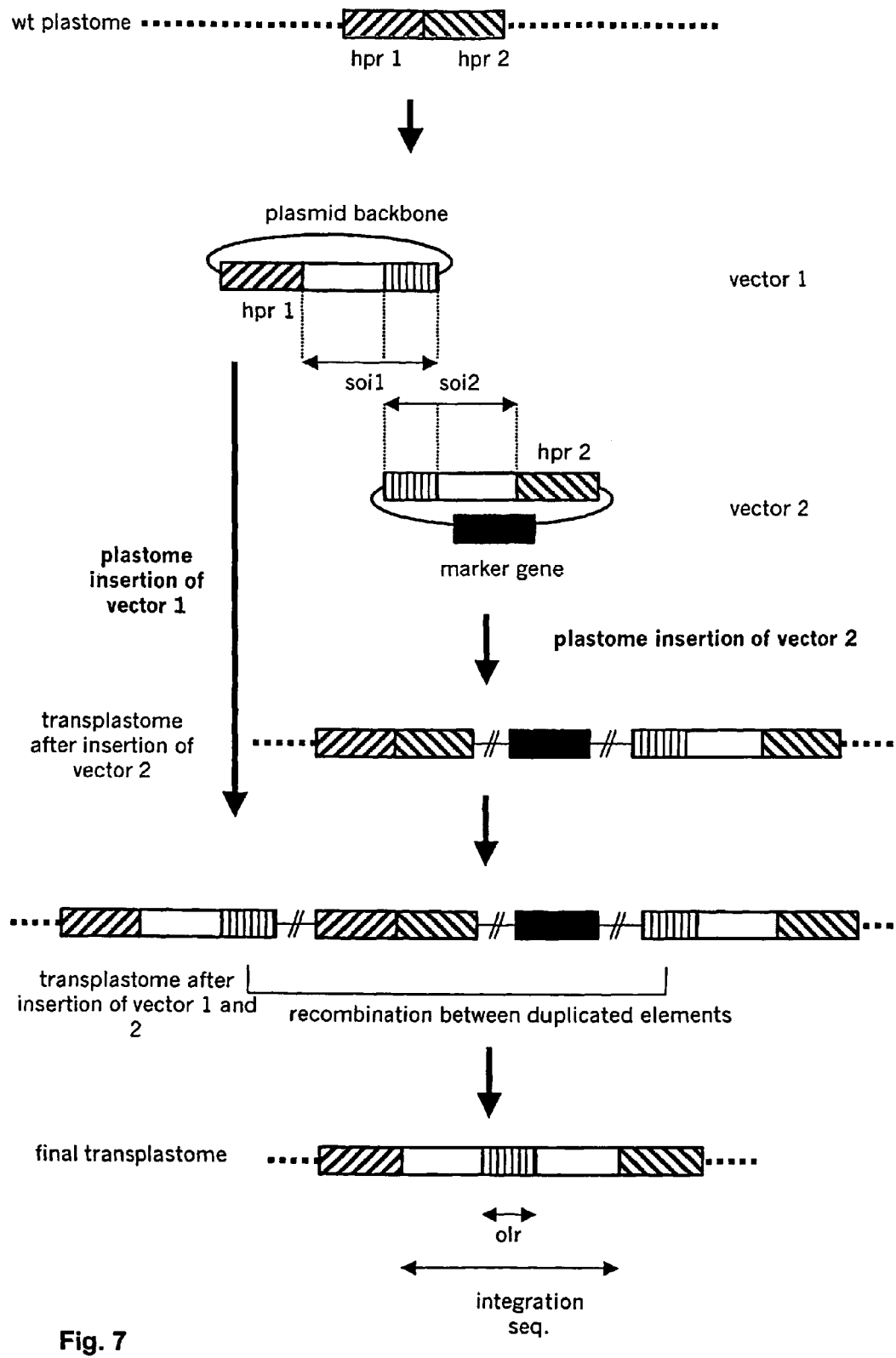

FIG. 7 Scheme showing the production of marker free transplastomic plants. Vector 2 contains a selectible marker gene outside of the sequence unit consisting of the homologous region and the sequence of interest. Integration of vector 1 and vector 2 leads to the transplastome after insertion of vector 1 and 2, that may be selected by transiently applying the suitable antibiotic. Recombination via the duplicated elements leads to excision of sequences including the marker gene. hpr, homologous plastome region; soi, sequence of interest; olr, overlapping region.

Figure 8:
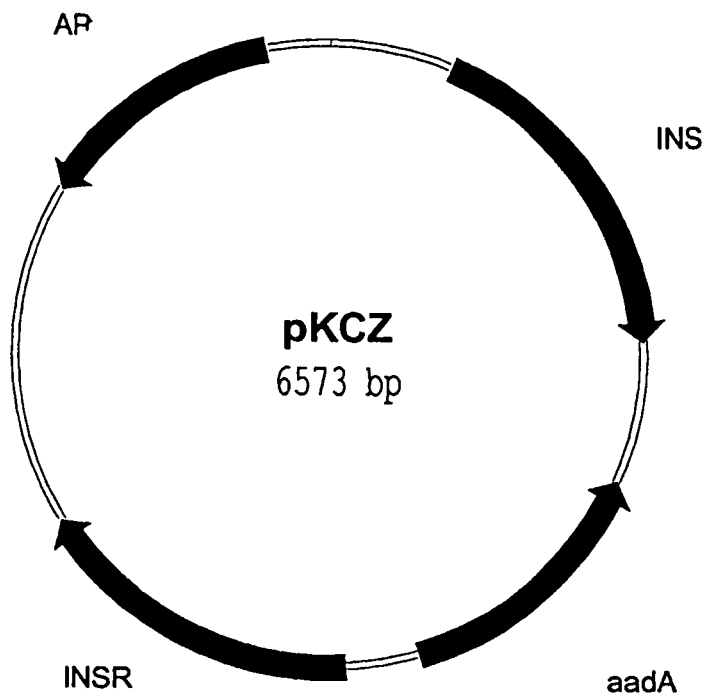

FIG. 8 Conventional plastid transformation vector pKCZ. aadA, aminoglycoside adenyl transferase; INSL, *N. tabacum* plastome sequence from bp 131106-132277; INSR, *N. tabacum* plastome sequence from bp 132278-133396; AP$^r$, β-lactamase.

Figure 9:
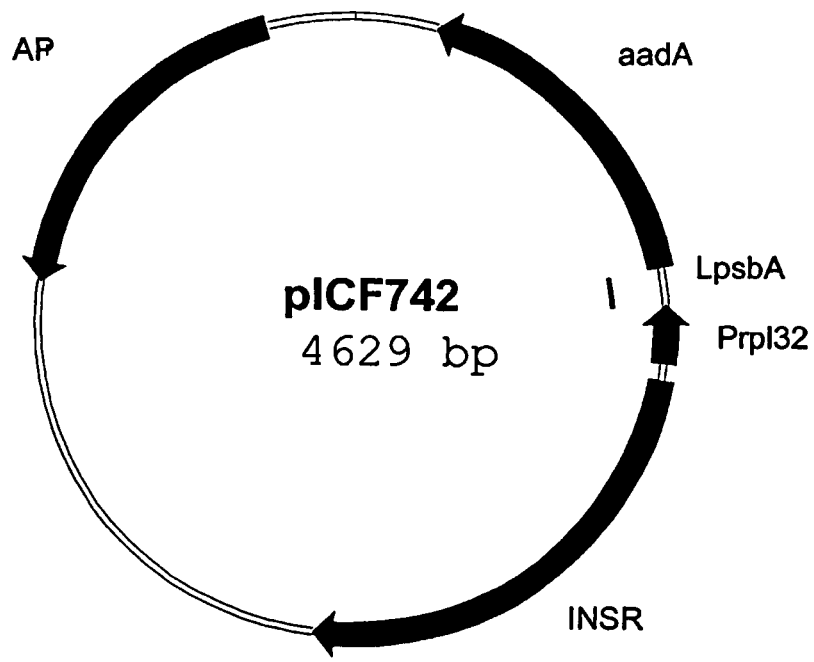

FIG. 9 Modular plastid transformation vector plCF742. aadA, coding sequence for aminoglycoside adenyl transferase; LpsbA, 5'-UTR from *N. tabacum* psbA gene; Prpl32, promoter from *N. tabacum* rpl32 gene; INSR, *N. tabacum* plastome sequence from bp 132279-133390; AP$^r$, β-lactamase.

Figure 10:
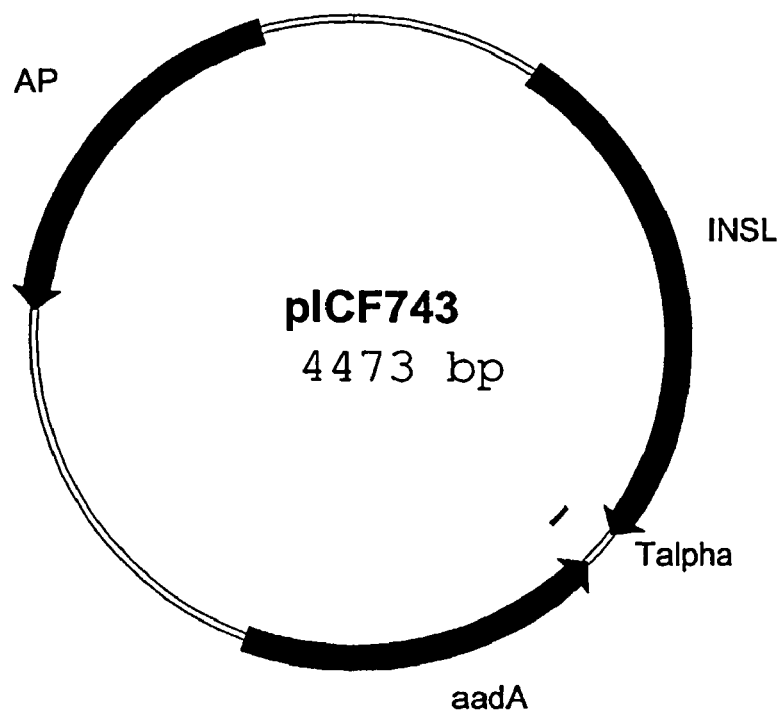
Figure 11:
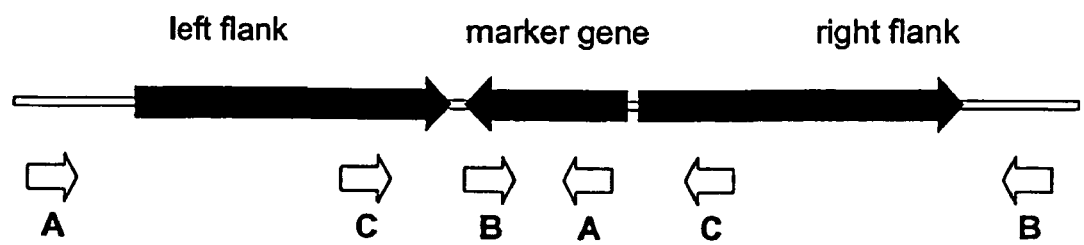

FIG. 10 Modular plastid transformation vector plCF743. aadA, coding sequence for aminoglycoside adenyl transferase; Talpha, alpha operon terminator from *E. coli*; INSL, *N. tabacum* plastome sequence from bp 131106-132277; AP$^r$, β-lactamase FIG. 11 Primer binding sites for PCR analysis of tobacco transformants from cotransformation of plCF742 and plCF743. A, primer pair A; B, primer pair B; C, primer pair C.

Figure 12:
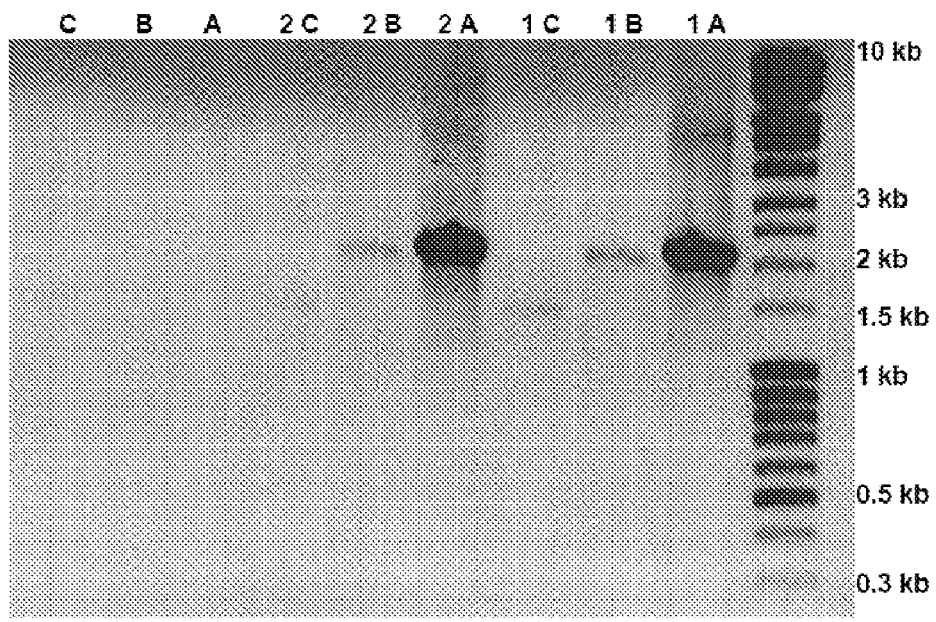

FIG. 12 PCR analysis of tobacco transformants from cotransformation of plCF742 and plCF743. 1, line 1; 2, line 2, A, primer pair A; B. primer pair B; C, primer pair C; left three lanes, control without DNA.

Figure 13:
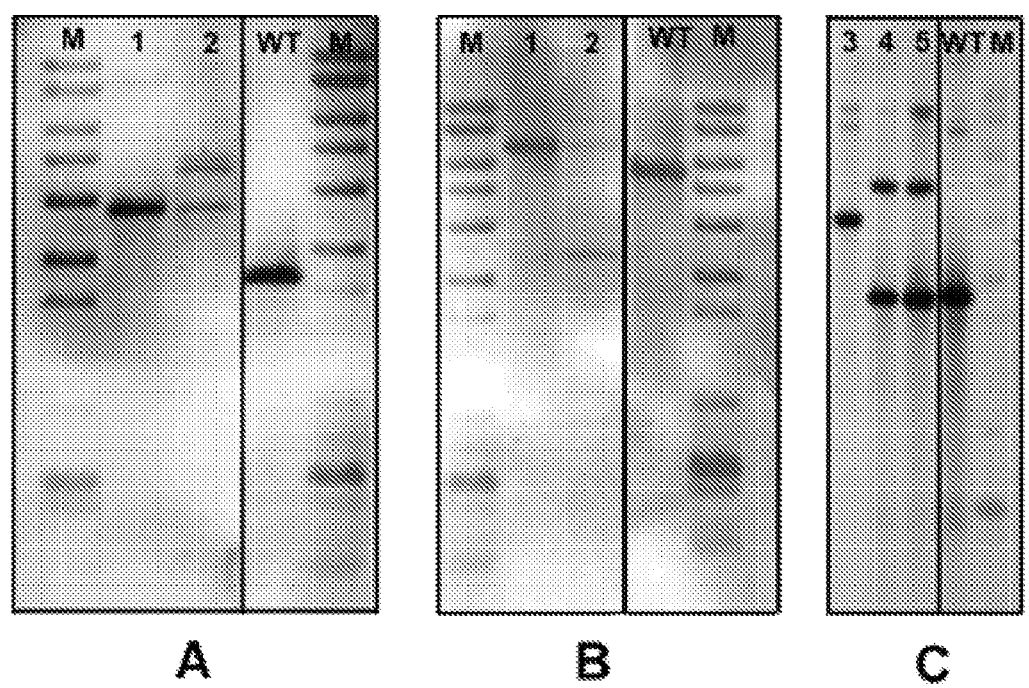

FIG. 13 Southern blot of tobacco transformants from cotransformation of plCF742 and plCF743. A and C, restriction with Bsp120I; B, restriction with AccIII. 1-5, line 1-5; M, marker lane (from top: 10 kb, 8 kb, 6 kb, 5 kb, 4 kb, 3 kb, 2.5 kb, 1.5 kb, 1 kb); WT, wild type control.

Figure 14:
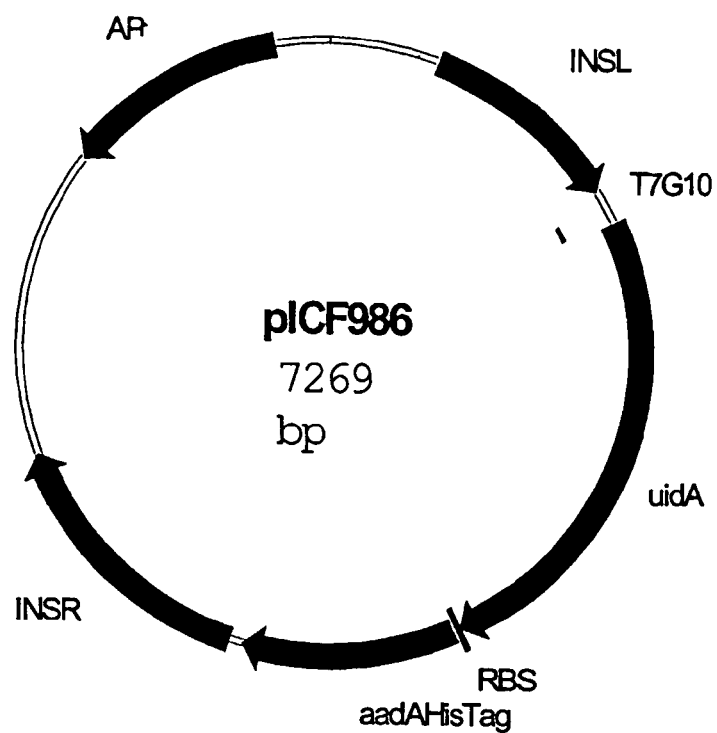

FIG. 14 Translation based plastid transformation vector plCF986. aadAHisTag, aminoglycoside adenyl transferase with C-terminal HisTag; INSL, *N. tabacum* plastome sequence complementary to bp 534 to bp 1336; INSR, *N. tabacum* plastome sequence complementary to bp 155370 to bp 533; AP$^r$, β-lactamase; T7G10, ribosomal binding site of gene 10 from phage T7; RBS, synthetic ribosomal binding site; uidA, β-glucuronidase.

Figure 15:
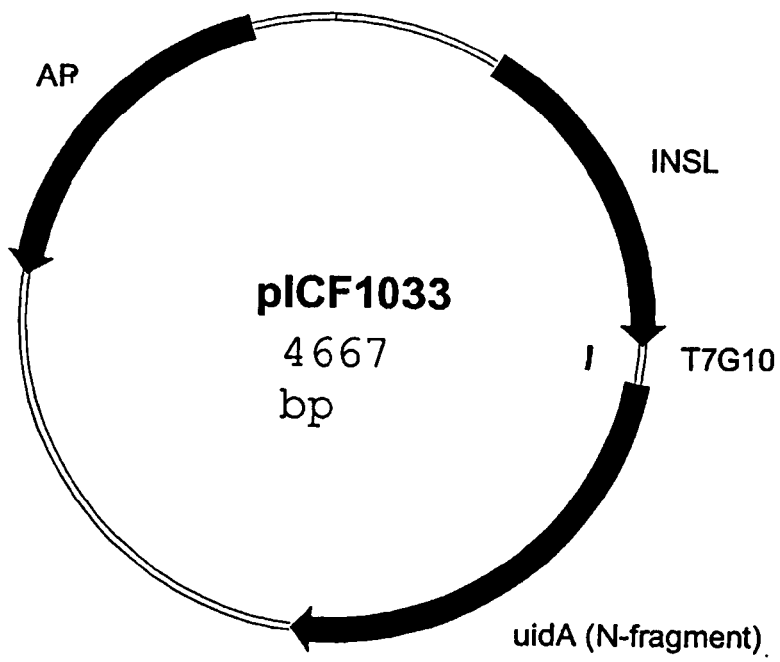

FIG. 15 Modular translation based plastid transformation vector plCF1033. INSL, *N. tabacum* plastome sequence complementary to bp 534 to bp 1336; AP$^r$, β-lactamase; T7G10, ribosomal binding site of gene 10 from phage T7; uidA (N-fragment), coding sequence for the N-terminal 373 aa of β-glucuronidase.

Figure 16:
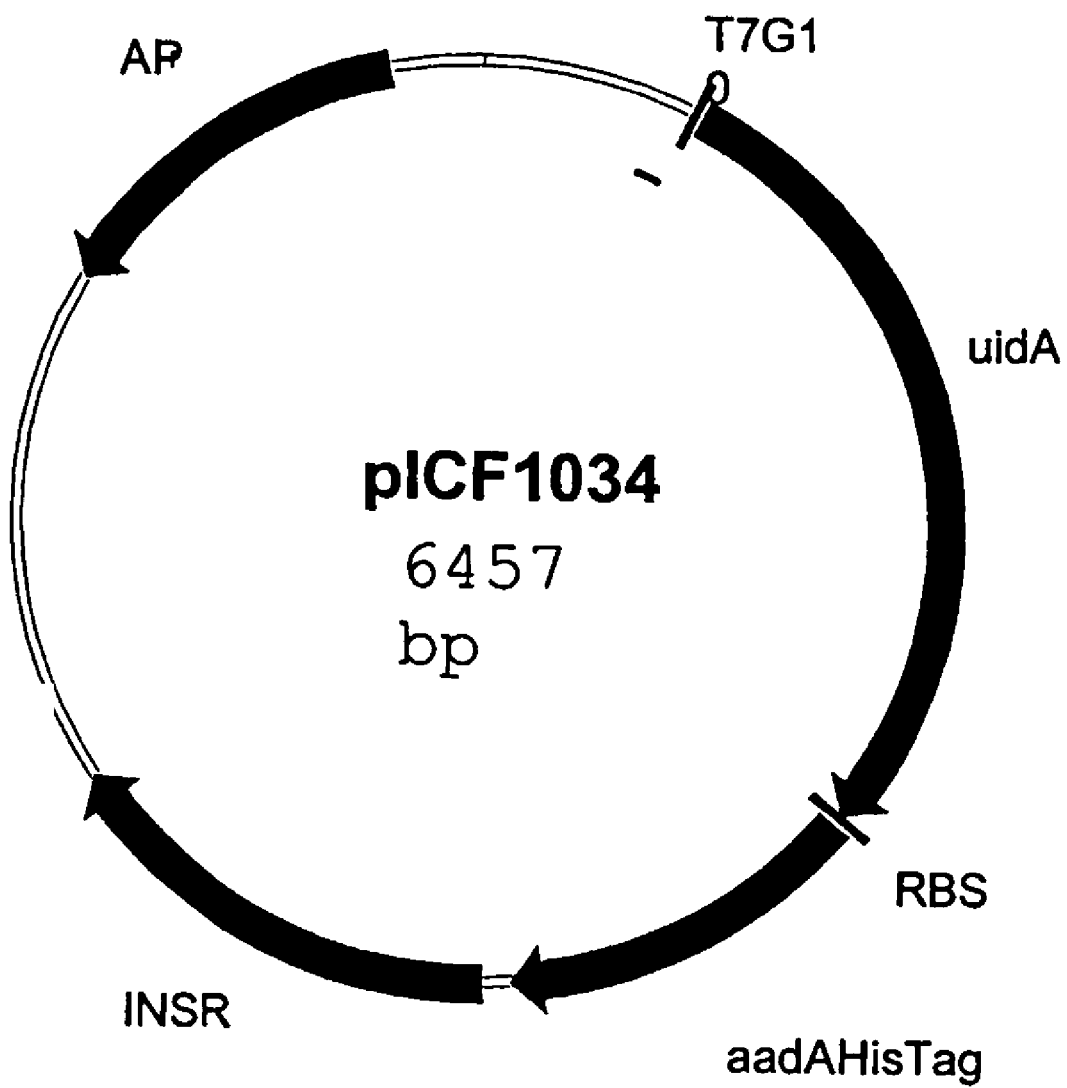

FIG. 16 Modular translation based plastid transformation vector plCF1034. aadAHisTag, aminoglycoside adenyl transferase with C-terminal HisTag; INSR, *N. tabacum* plastome sequence complementary to bp 155370 to bp 533; AP$^r$, β-lactamase; T7G10, ribosomal binding site of gene 10 from phage T7; RBS, synthetic ribosomal binding site; uidA, β-glucuronidase.

DETAILED DESCRIPTION AND PREFERRED EMBODIMENTS

When Using Conventional Plastid Transformation Vectors, a High Number of Regeneration Cycles is Required to Achieve Homoplastomic Transformants Conventional plastid transformation vectors usually contain an integration sequence which is not present in the wild type plant and that contains a selectable marker gene, one or more gene(s) of interest and regulatory elements such as promoters, 5'-UTRs, 3'-UTRs or spacer elements. In the vector, the integration sequence is flanked by two sequences homologous to the targeting plastome thus directing the position of the plastome integration. Insertion of the integration region into the target plastome is achieved by double reciprocal homologous recombination events. A simplified model suggests that integration occurs via two homologous recombination events, one event at each flank (FIG. 1). However, the actual molecular process is difficult to monitor and may be more complex involving intermediates. Experimental data obtained in our laboratory suggest that a first recombination event mediated by one of the two flanks leads to the integration of the full transformation vector, thus duplicating the flanking sequence (FIG. 2). Indeed, integration of the whole circular plasmid vector could be demonstrated by PCR and Southern Hybridization analysis (FIG. 3). At a different point in time a second recombination event can either cause a reversion of the first integration. Alternatively a second recombination between the two other duplicated flanking sequences causes excision of both the plasmid backbone and the duplicated fragments leaving the integrating sequence in the plastome (FIG. 2).

Using conventional plastid transformation vectors it takes several months to achieve homoplastomic plastid transformants, because up to 5 cycles of regeneration are necessary. A certain number of cell generations is required to convert the heteroplastomic cells into homoplastomic cells by segregation. Segregation into the desired configuration of the plastomes is driven by applying selective conditions.

The Vectors of this Invention Contain Not More than One Homologous Region

In contrast to conventional plastid transformation methods this invention discloses a process for producing transplastomic plants or plant cells, in which at least two different types of DNA molecules (e.g. transformation vectors) are introduced into plastids, preferably simultaneously. One homologous region for directing plastome integration is sufficient for each of said vectors, preferably each vector contains not more than one homologous region for directing plastome integration. Further, each vector contains a sequence of interest that is preferably not present in the wild type plant. The sequences of interest of said vectors will result in an integration sequence in the transplastomic plant obtained.

The integration sequence may contain foreign genes such as a marker gene or other sequences of interest. The marker gene may be any gene conferring resistance against an inhibitor such as an antibiotic resistance gene like aphA-6 or an herbicide resistance gene like bar or an visible marker gene like GFP.

Examples for other sequences of interest are any genes encoding or capable of expressing a useful protein like proinsulin, interferone, human serum albumin, human growth factors, peptides functioning as vaccines (such as a vaccine against hepatitis B) or genes for technical enzymes. However, the integration sequence to be generated may also consist in a deletion of plastid sequences, e.g. in order to generate specific mutants.

In the process of the invention, at least two DNA molecules (e.g. vectors) are released into the plastid, each containing a homologous region defining the integration site of the plastome. Preferably, said first or said second DNA molecule does not have more than one homologous region for directing plastome integration. More preferably, neither said first nor said second DNA molecule has more than one homologous region for directing plastome integration. This does not exclude the use of elements in the sequences of interest that have homology to plastome sequences like promoters or regulatory elements or other plastid sequences. If such elements homologous to plastid sequences are used in a sequence of interest, they may in principle also act as plastome integration sequences leading to undesired integration events. Such undesired integration events may in many cases be unproblematic, e.g. if they do not lead to stable transformants or to transformants that may be selected for by the selectable marker employed. Moreover, undesired transformants may be detected by molecular analysis e.g. of the integration sequence.

Elements homologous to plastid sequences are preferably significantly shorter than the homologous regions for plastome integration. This measure generally achieves a significantly lower recombination frequency for said homologous elements than for said homologous regions. Alternatively, such elements homologous to plastid sequences are preferably taken from plastome sequences located far away from the desired integration site of the DNA molecule to impede undesired recombination events.

The at least two different vector molecules are either released simultaneously or in two or more different transformation steps. Simultaneous transformation of at least two types of molecules is called co-transformation. Following co-transformation of the at least two vector molecules, the first regenerates containing plastids with the desired plastome modification appear after about 3 weeks of cultivation under adequate selection and culture conditions, depending on the transformation method applied. The method of co-transformation can be used with any transformation method which is suitable for generation of plastid transformants. Examples for suitable plastid transformation methods are the biolistic transformation, the PEG-mediated transformation, other transfection methods using chemical agents or the electric field mediated transfection of nucleic acids.

Alternatively, the at least two vector molecules may be applied in separated transformation steps. Consecutive transformation by at least two transformation steps leads to the same integration results observed during co-transformation.

If a third vector is used in addition to said first and said second DNA molecule, the third vector does not have to contain any homologous sequences derived from the target plastome, as long as the sequences of interest of the vectors contain an overlapping region sufficient for recombination. The same is true if more than three vectors are used.

Fragments of the marker gene may be located on different vectors, whereby the marker gene is assembled by recombination processes.

The Vectors of this Invention Enable the Generation of Homoplastomic Plants in a Very Short Time Surprisingly it was found that using the method described herein it is possible to recover homoplastomic plastid transformants after only two cycles of regeneration. Preferably, even one regeneration cycle is sufficient. In many cases, the regenerates recovered after transforming plant tissue or plant cells are homoplastomic even without any regeneration cycle being performed. In contrast to conventional plastid transformation vectors it is possible to obtain homoplastomic plants after a very short period of only several weeks. Therefore, the invention described herein offers an enormous acceleration of the process and a drastic reduction of the work needed for tissue culture.

Homoplastomic transformants do not contain any wild type plastomes. The presence of wild type plastomes can be monitored by methods such as Southern hybridization or PCR analysis. In transplastomic plant material recovered from primary regenerates which appear after transformation of plant tissue or cells, routine Southern analysis was performed to identify recombinant plastomes and to detect remaining wild type plastomes. 40% of the analyzed material from these primary regenerated does not contain any remaining wild type plastomes. Wild type plastomes could be eliminated from the other regenerates in only one step of sub-culture, whereas up to 5 cycles of sub-culture are needed using conventional transformation vectors.

A hypothetical mechanism for the introduction of foreign sequences according to this invention is described in FIG. 4. According to this model, one of the two vector molecules which contain a homologous region recombine with the respective plastome sequence. The homologous recombination event leads to the integration of the whole vector including the plasmid backbone. It also leads to a duplication of the homologous region. This process is reversible and may result in an excision of the recombinant sequence by homologous recombination mediated by the duplicated homologous regions unless the process is stabilized by another integration event. If the integration sequence contains a selectable marker gene which can be expressed, the vector will tend to stay integrated if selective pressure is applied. In the absence of any selective pressure, the plastome with one integrated vector is highly unstable. A second recombination event however may lead to the integration of at least one other molecule. If the other molecule contains another homologous region, a recombination with the respective homologous region of the plastome may occur. Alternatively, it is also possible that the recombination is mediated by any of the other repeated sequences such as the vector backbone or the overlapping region of the molecules. The second recombination event may occur between the free first vector and the integrated second vector (shown in FIG. 4), or between the free second vector and the integrated first vector (not shown in FIG. 4) or between the integrated first vector and the integrated second vector located on different plastome molecules (not shown in FIG. 4). Vector molecules that do not contain a homologous plastid region may only recombine with the other repeated sequences. In either case, an integration of the whole second vector molecule will appear. In cases where more than two vector molecules are used, all the molecules will integrate by one of the homologous regions. After integration of the different molecules into the plastome, a vast series of secondary intramolecular recombinations between any of the repeated sequences is possible. As a consequence all the repeated regions will be eliminated. The final result of these various recombination events is the generation of a continuous recombinant region referred to as integration sequence.

The Vectors of this Invention can be Used in a Combinatorial Approach

Expression in plastids is useful for a broad range of different purposes ranging from modified nutrient composition to high level expression of pharmaceuticals in plants. For that purpose it is necessary to obtain a set of interchangeable promoters and regulatory elements differing in strength and expression pattern. This allows to construct expression vectors for different purposes (weak, strong, constitutive or regulated expression etc.). The elements should be interchangeable to modify the expression level. For many cases it is favourable to use promoters, 5'-UTR and 3'-UTR from different genes because this excludes internal recombinations where the inserted gene is exchanged with an endogenous gene via identical 5'- and 3'-UTRs. On the other hand, 5'- and 3'-UTRs sometimes interact and together determine translation activities. It is therefore not always possible to estimate the effect of a particular combination. Modular vectors of this invention containing only the 5'- or 3'-regulatory elements allow an easy and fast way of combining different regulatory elements thus generating the desired expression cassette in the integration sequence. Vectors with different elements can be kept in libraries and can be combined at will. Moreover, if the optimal combination of different elements is not known, a mixture of different regulatory elements on different vectors can be used for transformation. The expression cassette with the desired properties is then obtained by selection of the transformant with desired properties, optionally followed by molecular analysis.

The Vectors of this Invention Avoid Surplus Cloning Work

Conventional plastid transformation vectors usually contain a selectable marker gene needed for the selection of the transformants, one or more gene(s) of interest and regulatory elements such as promoters, 5'-UTRs, 3'-UTRs or spacer elements. It needs a substantial effort to generate these highly complex plasmids consisting of many different elements. However, in different transformation vectors many identical elements are used. Using the method of this invention it is possible to construct a vector that contains these identical elements, such as a homologous region, a selection marker gene and regulatory elements in one molecule. The at least one other transformation vector carries the different sequences of interest to be introduced into the plastome. Combining the first vector molecule with any other adequate vector containing any of the desired sequences reduces the complexity of the plasmids and consequently the effort to construct these molecules.

The Vectors of this Invention Are Smaller than Conventional Plastid Transformation Vectors and Thus Allow for the Insertion of More Sequences of Interest Construction of transformation vectors is frequently restricted by insert size limitations. Conventional plastid transformation vectors usually contain two homologous regions, a selectable marker and regulatory elements. Therefore, only a limited number of additional sequences can be introduced. However it may be desirable to engineer complex metabolic pathways in the plastids, which depend on the expression of several different enzymes. As the vectors of the invention contain less compulsory sequences compared to conventional vectors, it is possible to insert longer sequences of interest. In addition, more than two transformation vectors with overlapping regions may be used in order to introduce even larger integration sequences which are assembled in the plastids.

The Vectors of this Invention Avoid Problems Derived from Toxic Effects of Some Sequences on the Bacteria Used for Cloning Genetic engineering can use the potential of plants as self-reproducible factories for the production of a vast number of organic substances. It has been shown, that an economic and environmentally friendly production of substances like enzymes, diagnostics or therapeuticals in plants is possible.

In some cases however, the genes to be introduced into plants can have toxic effects on the bacteria used for cloning. In these cases, construction of the transformation vector is restricted. An example for a sequence that has toxic effects on bacteria is the gene HbsAg encoding a surface antigen of the Hepatitis B virus. Expression of the gene in plant plastids would be desirable, because it would constitute a source for a vaccine e.g. against Hepatitis. However cloning of the full gene including the regulatory elements used in conventional transformation vectors is restricted, because the plastid regulatory elements are also active in bacteria. Using the vectors of this invention it is possible to split the full expression cassette of a gene like HbsAg between two molecules in a way that none of the vectors alone contains an expressible cassette. Using that approach the restrictive effects of genes toxic for bacteria are overcome.

The Vectors of this Invention Allow the Generation of Resistance Marker Free Plants A method for obtaining plastid transformants which are devoid of resistance marker genes is highly desirable in order to prevent unwanted spread of the marker gene into the environment. Conventional plastid transformation vectors usually contain a suitable resistance marker gene which is necessary for the selection of the transformants. The resistance marker is located in the integration sequence of the transformation vector and leads to a stable plastome integration of the resistance gene in the final plant.

Using the process and vectors described in this invention it is possible to place such resistance marker genes outside the sequence unit consisting of the homologous region and the sequence of interest. Following transformation an integration of the full transformation vector occurs (FIG. 2), which leads to the transient insertion of the selection marker in the plastome. The recombination event causes a duplication of the homologous region. Transformed cells can be selected for on a medium containing the appropriate inhibitor during that stage. As soon as the plant material is transferred to inhibitor-free medium, the selective pressure for the maintenance of the full vector integration is released. Further recombination events (as described in FIG. 4) mediated by the previously generated duplicated homologous regions lead to an excision of the selection marker gene. Consequently, the final plant does not carry the resistance marker gene used for selection of the transformants.

The resistance marker gene may also be split in two or more overlapping fragments, each located on a different vector, whereby the resistance is only mediated if the fragments recombine to the complete expressible marker gene.

In some embodiments of the invention, intron splicing may be used for processing a primary transcript to obtain a desired secondary transcript, e.g. for correct translation of a protein of interest. For this purpose, a 5' part of an intron may be included in said first sequence of interest and a 3' part of an intron may be included In said second sequence of interest (or vice versa), whereby a functional intron is formed upon formation of said integration sequence and transcription in plastids. Said 5' and said 3' intron parts may be derived from a natural intron or derivatives thereof. Self-splicing introns like group I and group II introns have the ability to splice themselves out of pre-mRNA. Both group I and group II introns are capable of splicing (including trans-splicing) in artificial systems (Been et al., 1986, *Cell*, 47, 207-216; Jacquier et al., 1986, *Science*, 234, 1099-1194; Jarrell et al., 1988, *Mol. Cell Biol.* 8, 2361-2366). Trans-splicing was also found for group II introns in split genes of chloroplasts (Kohchi et al., 1988, *Nucl. Acids Res.*, 16, 10025-10036), and for a group I intron in an artificial split gene in *Escherichia coli* (Galloway-Salvo et al., 1990, *J. Mol. Biol.*, 211, 537-549). Group I introns were first discovered in *Tetrahymena thermophila* rRNA (Cech, T. R., 1990, *Annu. Rev. Biochem.*, 59, 543-568). They require a U in the target sequence immediately 5' of the cleavage site and bind 4-6 nucleotides on the 5' side of the cleavage site. There are over 75 known members of this group up to now. They were found also in fungal and plant mitochondria (Richard & Dujon, 1997, *Curr. Genet*, 32, 175-181; Cho et al., 1998, *Proc. Natl. Acad. Sci. USA*, 95, 14244-14249), chloroplasts (Turmel et al. 1993, *J. Mol. Biol.* 232, 446-46), phage T4 (Galloway et al., 1990, J. Mol. Biol., 211, 537-549), blue-green algae, and other organisms. Ribozymes engineered on the basis of group I Tetrahymena introns (U.S. Pat. No. 6,015,794; Ayre et al., 1998, *Proc. Nail. Acad. Sci. USA*, 96, 3507-3512) or group II intron-mediated trans-splicing (Mikheeva & Jarrell, 1996, *Proc. Natl. Acad. Sci. USA*, 93, 7486-7490; U.S. Pat. No. 5,498,531) may be used for the present invention.

Preferred embodiments of the invention are now described in detail.

Embodiment 1

Co-transformation of Two Vectors

Plastids are transformed simultaneously with said first and said second DNA molecule referred to as modular vectors (FIG. 5). Vector 1 (said first DNA molecule) contains one region homologous to a plastome region (said first homologous region). The integration of sequences of interest should take place downstream of this plastome region. The homologous region typically has a length of 500 to 1000 bp. If desirable, shorter or longer sequences may also be used. On vector 1, the first sequence of interest is located downstream of this homologous region. The upstream part of the integration sequence is contained in the first sequence of interest downstream of this homologous region.

Vector 2 (said second DNA molecule) contains one region homologous to a plastome region (said second homologous region). The integration of sequences of interest should take place upstream of this plastome region. The homologous region typically has a length of 500 to 1000 bp, too. On vector 2, the second sequence of interest is located upstream of this homologous region. The downstream part of the integration sequence is contained in the second sequence of interest upstream of this homologous region.

In this preferred embodiment, the two homologous regions of the two vectors are present next to each other on the plastome without intervening sequences. A sequence segment of the downstream region of the first sequence of interest on vector 1 is homologous to a sequence segment of the upstream region of the second sequence of interest on vector 2. This homologous sequence segment is also referred to as overlapping region. Typically, this homologous sequence segment has a length of 500 to 1000 bp. After the recombination events described in the invention, the cotransformation of the two vectors results in a continuous integration sequence integrated between the two plastome regions used as homologous regions. Typically, each vector only contains a part of the integration sequence.

It has been shown that recombination also takes place with longer or shorter homologous regions, but a length of 500 to 1000 bp is sufficient for efficient recombination and can be amplified easily with standard PCR procedures.

The marker gene for selecting transformants can be located as two fragments on the two vectors, i.e. one fragment on each vector. The marker gene may be split into two fragments in several ways. Non limiting examples for that splitting are:

a) The promoter and 5'-UTR are located on vector 1. The coding sequence is located on the overlapping region of vector 1 and vector 2. The 3'-UTR is located on vector 2.

b) The promoter, 5'-UTR and 5'-part of the coding sequence are located on vector 1. The middle part of the coding sequence is located on the overlapping region of vector 1 and vector 2. The 3'-part of the coding sequence and the 3'-UTR are located on vector 2.

If the homologous regions on the vectors are chosen such that the integration sequence is integrated in a plastome region transcribed by an endogenous promoter, it is not necessary to include a promoter in front of the marker gene. Besides the marker gene, additional gene(s) of interest may be included either in the sequences of interest of vector 1 or vector 2 or both.

Embodiment 2

Co-transformation of Fragmented Genes on Two Vectors

Since plastids and bacteria have similar expression systems, it is sometimes difficult or even impossible to clone plastid transformation vectors in *E. coli*, if genes are involved the gene products of which are toxic for *E. coli*. This problem is solved by splitting such a gene into 2 or more fragments as described for the marker gene in embodiment 1. On each vector, the toxic gene is then present as an incomplete gene or fragment that is non toxic. Plastids are then transformed simultaneously with two modular vectors as described in embodiment 1, whereupon the functional complete gene of interest is reassembled within the plastids.

Embodiment 3

Co-transformation of Three Vectors

For some purposes it is advantageous to distribute an integration sequence necessary for stable plastid transformation on three vectors (FIG. 6). Non limiting examples are: insertion of very long integration sequences (e.g. gene clusters), serial construction of transformation vectors etc.

Vector 1 contains a first region homologous to the plastome region and a first sequence of interest downstream thereof. The integration of the integration sequence should take place downstream of this plastome region. Downstream of the first homologous region, the upstream part of the integration sequence is present in the first sequence of interest.

Vector 2 contains a second region homologous to the plastome region and a second sequence of interest. The integration of the integration sequence should take place upstream of this plastome region. Upstream of this homologous region, the downstream part of the integration sequence is present in the second sequence of interest. As described for embodiment 1, the homologous sequences are typically 500 to 1000 bp long, but are not limited to this length.

Vector 3 contains a third sequence of interest, the upstream part of which is homologous to the sequence of interest of vector 1 and the downstream part is homologous to a sequence of interest of vector 2. Vector 3 may or may not contain the complete integration sequence which should be integrated into the plastome.

Embodiment 4

Selectable Marker-free Transplastomic Plants

If the selectable marker gene is located outside of the region designed for integration, the marker gene will be present in the full vector integration intermediates (FIG. 7). When selection pressure is released, the marker gene is excised together with vector sequences. The homologous plastid sequences and sequences of interest are arranged as described in embodiment 1. Contrary to embodiment 1, the marker gene is not included in the sequence of interest. Instead it is located elsewhere on vector 1 or vector 2. Preferably, the marker gene is separated from the unit consisting of the homologous region and the sequence of interest by vector sequences. Preferably, vector 1 and vector 2 each contains a marker gene in this fashion, whereby these marker genes are different, e.g. aadA and aphA6. Selection is then carried out by using a combination of the two respective antibiotics e.g 500 mg/A spectinomycin +25 mg/l kanamycin. Alternatively, a fragment of a marker gene is located on vector 1 and the other fragment of the marker gene is located on vector 2, whereby both fragments are outside the above-defined unit. It is a prerequisite then that both fragments share a homologous segment (overlapping region) which allows recombination of both fragments to assemble a complete functional marker gene after insertion of both vectors into the plastome. As only a fraction of the possible recombination events yields a functional marker, the selection pressure maintains intermediates containing said functional marker. When selection pressure is removed, the marker gene together with remaining vector sequences will be removed by recombination due to repetitive vector sequences.

Embodiment 5

Selectable Marker-free Transplastomic Plants

Resistance marker free plants can be obtained by using modular vectors which contain homologous sequence elements 5' of the resistance marker gene on the first DNA molecule and 3' of the resistance marker gene on the second DNA molecule, whereas the resistance marker gene or a fragment thereof is present on said first and said second DNA molecule. After the recombination events described in FIG. 4 the resistance marker gene flanked by two homologous sequence elements is inserted into the plastome. The presence of the selection marker in the insertion sequence can be maintained by selective pressure. When the plant material is transferred to inhibitor-free medium, the selective pressure for the maintenance of the resistance marker gene is released. A further recombination event mediated by the two homologous sequence elements may lead to an excision of the selection marker gene. Consequently, the final plant does not carry the resistance marker gene used for selection of the transformants.

The process of the invention is preferably carried out with crop plants which include gymnosperms (such as pine, spruce and fir etc.) and angiosperms. Angiosperms are more preferred. Angiosperms include monocotyledonous plants like maize, wheat, barley, rice, rye, Triticale, sorghum, sugar cane, asparagus, garlic, palm tress etc., and dicotyledonous plants like tobacco, potato, tomato, rape seed, sugar beet, squash, cucumber, melon, pepper, Citrus species, egg plant, grapes, sunflower, soybean, alfalfa, cotton etc. Solanaceae are most preferred (e.g. potato, tomato, pepper, egg plant, tobacco).

EXAMPLES

Molecular biology methods used in this invention are well known in the art and are described for example by Sambrook et al. (1989) Molecular cloning and by Ausubel et al. (1999) Short protocols in Molecular Biology.

Example 1

PCR Analysis of Complete Vector Integration (Via One Flank) into the Plastid Genome Plastid Transformation Vector pKCZ pKCZ is a conventional plastid transformation vector where the selection marker is cloned between the two flanks used for homologous recombination. The vector is designed to make a neutral insertion between trnR and trnN in the inverted repeat region of the tobacco plastid genome (Zou, 2001). pKCZ comprises two flanking sequences for homologous recombination (corresponding to *Nicotiana tabacum* plastome sequences 31106-132277 and 132278-133396, according to GenBank accession number Z00044) and an aadA plastid expression cassette under control of the 16s rRNA promoter (Koop et al., 1996). A schematic drawing of the plasmid construct is shown in FIG. 8.

Generation of Primary Transformants and Subsequent Selection for Homoplastomic Lines Particle gun-mediated plastid transformation and subsequent selection were carried out as described in Mühlbauer et al, 2002. Selection of transformants was based on the resistance to the antibiotics spectinomycin/streptomycin, conferred by the aadA gene product. In order to amplify transformed plastid genomes and to eliminate wild-type genomes, the primary transformants (cycle-0) were subjected to several additional rounds of regeneration (from small leaf explants) on selective media containing spectinomycin (here designated as cycle-I, cycle-II etc).

Analysis of Primary Transformants by PCR

Plastid transformants (cycle-0) were identified by PCR using total DNA isolated with the DNeasy Plant Mini Kit (QIAGEN, Hilden, Germany). To determine the presence of the aadA gene the primers oSH81 (SEQ ID NO:3) (5'-CTAT-CAGAGGTAGTTGGCGTC-3') and oFCH60 (SEQ ID NO:1) (5'-CACTACATTTCGCTCATCGCC-3') were used. The PCR program was as follows: 3 min at 94° C., 1 cycle; 45 sec at 94° C., 45 sec at 55° C., 2 min at 72° C., 30 cycles; final extension at 72° C. for 10 min. The results showed that 48 lines from 54 analysed (6 bombarded leaves) gave the expected amplification product of 504 bp. To prove correct integration of the aadA cassette within the tobacco plastome primers oSH58 (SEQ ID NO:2) (5'-TATTCCGACTTC-CCCAGAGC-3') and oFCH60 (SEQ ID NO:1) (5'-CACTA-CATTTCGCTCATCGCC-3') were used. Primer oSH58 is located outside (downstream) of the right flank of pKCZ in the tobacco plastome and in combination with oFCH60 can only give the expected product of 2106 bp upon integration of the aadA expression cassette between trnR and trnN in the inverted repeat. The PCR program was as follows: 5 min at 94° C., 1 cycle; 45 sec at 94° C., 45 sec at 55° C., 3.5 min at 72° C., 35 cycles; final extension at 72° C. for 7 min. All 48 of the aadA PCR positive lines showed the expected right-flank-aadA product of 2106 bp.

Ten of the cycle-0 transformants (1:1, 1:2, 1:3, 1:4, 1:5, 2:1, 2:4, 2:5 2:6 and 2:7) were selected for further analysis.

PCR Analysis of Transformants Containing Completely Integrated Vectors

Normally, the production of stable plastid transformants is thought to occur via two simultaneous recombination events occurring between the left and right flanks of the transforming molecule and the plastome (as depicted in FIG. 1). An alternative mechanism is presented in FIG. 2. Here, complete integration of the vector occurs first, via recombination with one flank only (either left or right) with the plastome, resulting in the generation of a hypothetical unstable intermediate. Subsequent additional recombination events can then take place between the duplicated flanks in this molecule to generate either the wild-type situation or a stably integrated aadA cassette. In order to test for this possibility, PCR was performed using primers oSH3 (SEQ ID NO:4) (5'-GGCATCA-GAGCAGATTG-3') and oSH58 (SEQ ID NO:2) (5'- TATTC-CGACTTCCCCAGAGC-3'). Primer oSH3 is located within the vector backbone of pKCZ (pUC18) and primer oSH58 is located outside (downstream) of the right flank of pKCZ in the tobacco plastome. A product of 2638 bp can only be obtained with these two primers when complete pKCZ integration has occurred as shown in FIG. 2. No PCR product of the expected size will be obtained from the wild type plastome fragment (comprising left and right flanks) since the binding site for oSH3 is absent. The PCR program was as follows: 5 min at 94° C., 1 cycle; 45 sec at 94° C., 45 sec at 55° C., 3.5 min at 72° C., 35 cycles; final extension at 72° C. for 7 min. Nine of the 10 cycle-0transformants analysed showed a PCR product of 2.6 kb which would be consistent with complete integration of pKCZ into the plastid genome within these lines (FIG. 3A). No product of the correct size was observed in the wild type control or in sample 1:1. Since complete integration of pKCZ results in the formation of an unstable intermediate it is to be expected that with increasing time additional recombination events between the duplicated flanks in this molecule will lead to either the wild-type situation or a stably integrated aadA cassette. As such DNA samples prepared from cycle-I and cycle-II plant material were analysed by PCR with primers oSH3 and oSH58. If the model presented in FIG. 2 is correct the probability of amplifying the 2638 bp band with primers oSH3 and oSH58 should be reduced with each regeneration cycle on selection. The results suggest that this is indeed the case since only 5 of the 10 cycle-I lines analysed gave a strong PCR product of the expected size (FIG. 3B). Furthermore, in cycle-II the number of lines showing clear amplification of the expected 2638 bp band was further reduced.

The model presented in FIG. 2 also predicts that all cycle-II lines which are negative for complete vector integration should still show PCR signals consistent with a stably integrated aadA cassette due to the molecular rearrangements previously described. To prove integration of the aadA cassette within the tobacco plastome primers oSH58 (SEQ ID NO: 2) (5'-TATTCCGACTTCCCCAGAGC-3') and oFCH60 (SEQ ID NO: 1) (5'-CACTACATTTCGCTCATCGCC-3') were used. The PCR program was as follows: 5 min at 94° C., 1 cycle; 45 sec at 94° C., 45 sec at 55° C., 3.5 min at 72° C., 35 cycles; final extension at 72° C. for 7 min. All 10 of the cycle-II transformants show the expected right-flank-aadA product of 2106 bp (FIG. 3E) which would be consistent with the scenario shown in FIG. 2.

Example 2

Construction of Overlapping Modular Vectors

Modular vector plCF742 (FIG. 9) comprises the right flanking region homologous to the tobacco plastome, the tobacco rpl32 promoter, the tobacco psbA-5'-UTR and the aadA marker gene.

The right flanking region was amplified from tobacco plastid DNA (bp 132279 to bp 133390 of the *N. tabacum* plastome) with modifying primers 5'-TGGAGCTCGAATTGC-CGCGAGCAAAGATATTAATG -3'(SEQ ID NO: 5) and 5'-TACGAATTCAAGAGAAGGTCACGGCGAGAC-3' (SEQ ID NO: 6), introducing an SacI recognition site at the 5'-end and an EcoRI recognition site at the 3'-end. The PCR product was purified and digested with SacI and EcoRI and legated into a pUC18 plasmid which was digested with the same enzymes. The rp132 promoter was amplified from tobacco plastid DNA (bp 113917 to bp 114055 of the *N. tabacum* plastome) with modifying primers 5'-GACCCTG-CAGGCAAAAAATCTCAAATAGCC -3'(SEQ ID NO: 7) and 5'-CGGGATCCGATTTTTCTTTAGACTTCGG-3' (SEQ ID NO: 8), introducing a PstI recognition site at the 5'-end and a BamHI recognition site at the 3'-end. The PCR product was reamplified with modifying primers 5'- CGG-GATCCGATTTTTCTTTAGACTTCGG-3'(SEQ ID NO: 9) and 5'- CGAGCTCCACCGCGGTGGCGGCCCGTC-GACCCTGCAGGCAAAAAATCTC-3'(SEQ ID NO: 10) to introduce a new multi cloning site containing a SacI recognition site at the 5'-end. The resulting PCR product was digested with BamHI and SacI and legated into the similar restricted pUC18 vector containing the right flanking region. The psbA-5'-UTR was amplified from tobacco plastid DNA (complementary to bp 1598 - bp 1680 of the *N. tabacum*plastome) with modifying primers 5'-CGGGATCCAAAAAGC-CTTCCATTTTCTATTT-3' (SEQ ID NO: 11) and 5'- TTG-CAGCCATGGTAAAATCTTGGTTTATT-3' (SEQ ID NO: 12) introducing a BamHI recognition site at the 5'-end and a NcoI recognition site at the 3'-end. The PCR product was digested with NcoI and BamHI. The aadA sequence from *E. coli* was amplified from plasmid pFaadAII (Koop et al., 1996) with the modifying primer 5'-TGAATTCCCATGGCTCGT-GAAGCGG-3' (SEQ ID NO: 13) and 5'-GGTGATGAT-GATCCTTGCCAACTACCTTAGTGATCTC -3' (SEQ ID NO: 14) introducing a NcoI recognition site at the 5'-end. The PCR product was reamplified with primers 5'- TGAATTC-CCATGGCTCGTGAAGCGG-3' (SEQ ID NO: 15) and 5'-GCTCTAGATTAGTGATGATGGTGATGAT-GATCCTTGCC-3' (SEQ ID NO: 16) to introduce a His-tag and XbaI recognition site at the 3'-end. The PCR product was digested with NcoI and XbaI. The pUC18 vector containing the right flanking region and the rpl32 promoter was digested with BamHI and XbaI and legated with the digested psbA-5 '-UTR and the digested aadA. The resulting plasmid was digested with XbaI and NdeI to remove the remaining pUC18 multicloning site. The digested plasmid was purified on an agarose gel. The band at 4600 bp was extracted purified and the ends filled in with Klenow polymerase. The plasmid was then relegated, resulting in pICF742.

Modular vector pICF743 (FIG. 10) comprises the left flanking region homologous to the tobacco plastome, the alpha operon terminator from *E. coli* and the aadA marker gene.

The multicloning site of pUC18 between PaeI and SapI was removed and replaced by a new multicloning site consisting of (from 5' to 3') BamHI, KpnI, XbaI and NcoI. The left flanking region was amplified from tobacco plastid DNA (bp 131106 to bp 132277 of the *N. tabacum* plastome) with modifying primers 5'-GATGGATCCTTGCTGTTGCATC-GAAAGAG-3' (SEQ ID NO: 17) and 5'-CACTGGTAC-CCGGGAATTGTGACCTCTCGGGAGAATC-3' (SEQ ID NO: 18), introducing a BamHI recognition site at the 5'-end and a KpnI recognition site at the 3'-end. The PCR product was purified and digested with BamHI and KpnI and legated into the pUC18 plasmid with new multicloning site, which was digested with the same enzymes. The resulting plasmid was digested with KpnI and XbaI. The digested vector was legated with the single strand oligonucleotide 5'-GAT-GTCTAGAAGCAACGTAAAAAAACCCGC-CCCGGCGGGTTTTTTTATACCCGTAG-TATCCCCAGCGGCCGCGGTAC-3'(SEQ ID NO: 19), coding for the *E. coli* alpha operon terminator. The complementary strand was filled in with Taq polymerase, digested with XbaI and relegated. The resulting vector was digested with NcoI and XbaI and legated with the aadA PCR product from pICF742, resulting in vector pICF743.

12.5 µg of vector pICF742 and 12.5 µg of vector pICF743 were mixed, loaded on gold particles and transformed in *N. tabacum* plastids by particle bombardement as described in Mühlbauer et al, 2002. Selecton of transformants was based on the resistance to the antibiotics spectinomycin/streptomycin, conferred by the aadA gene product. In order to amplify transformed plastid genomes and to eliminate wild-type genomes, the primary transformants (cycle-0) were subjected to several additional rounds of regeneration (from small leaf explants) on selective media containing spectinomycin (here designated as cycle-I, cycle-II etc).

Two spectinomycin/streptomycin resistant calli from cycle-0 were analysed by PCR to verify the transformation. Three different primer pairs were used (FIG. 11):

A) 5'-CAGACTAATACCAATCCAAGCC-3' (SEQ ID NO: 20) (binding outside the left flanking region at the *N. tabacum* plastome) and 5'-CTATCAGAGGTAGT-TGGCGTC-3' (SEQ ID NO: 21) (binding at the marker gene).

B) 5'-CACTACATTTCGCTCATCGCC-3' (SEQ ID NO: 22) (binding at the marker gene) and 5'-TATTCCGACT-TCCCCAGAGC-3' (SEQ ID NO: 23) (binding outside the right flanking region at the *N. tabacum* plastome)

C) 5'-CATCAATACCTCGGTCTAG-3' (SEQ ID NO: 24) (binding at the left flanking region) and 5'-ACACATAG-TATGCCCGGTC-3' (SEQ ID NO: 25) (binding at the right flanking region).

PCR with all three primer showed amplificates, proving the integration of both vectors resulting in one continuous integrated region (FIG. 12). The calculated amplificate sizes are 2139 bp (A), 2035 bp (B) and 1450 bp (C) which fits well with the observed sizes. Remarkably no wild type signal (290 bp) is visible with primer pair C, indicating that even in such an early stage no untransformed is present. Five spectinomycin/streptomycin resistant calli from cycle0 and cycle-I were then analysed in three independent Southern blot experiments (FIG. 13). Two lines showed the presence of solely the complete correct integrated aadA gene (line 1 and line 3: 3.8 kb for Bsp120I restriction and 6.7 kb for AccIII restriction). One line (line 2) showed the integraded aadA gene and an additional signal (4.9 kb for Bsp120I restriction and 3.5 kb for AccIII restriction) corresponding to an intermediate recombination. Two lines (line 4 and line 5) showed the intermediate recombination signal (4.9 kb for Bsp120I restriction) and the wild type signal (2.6 kb for Bsp120I restriction). This result indicates that 2 out of the 5 analysed lines reached the homoplastomic integration status within a very short time.

Example 3

Construction of Overlapping Modular Translation Based Vectors

Translation based vectors do not contain own promoter elements but rely on endogenous promoter elements of the plastome upstream of the desired integration site.

This example presents two modular vectors (pICF1033 and pICF1034) which in combination substitute a translation based vector (pICF986) which could not be constructed despite several attempts because of the high expression level in *E. coli*. The ribosomal binding site (T7G10) used mediates high expression in plastids as well as in *E. coli*. Although the vectors do not contain plastid promoter elements, the left flanking region necessary for homologous recombination contains sequence elements which have promoter activity in *E. coli*.

Contrary to pICF986 (FIG. 14) the two modular vectors pICF1033 (FIG. 15) and pICF1034 (FIG. 16) could be constructed without problems. As the modular vector containing the left flanking region (pICF1033) does not contain the complete gene to be expressed, this modular vector avoids the problematic high expression in *E. coli*.

Modular vector pICF1033 contains the left flanking region homologous to the tobacco plastome, the ribosomal binding site of gene 10 from phage T7 and the N-terminal part of the uidA reporter gene.

The left flanking region was amplified from tobacco plastid DNA (complementary to bp 534 to bp 1336 of the *N. tabacum* plastome) with modifying primers 5'- TATAGGGCCCAGC-TATAGGTTTACATTTTTACCC-3' (SEQ ID NO: 26) and 5'-GTCCTGCAGTTATCCATTTGTAGATGGAGCTTCG-3' (SEQ ID NO: 27), introducing a Bsp 120I recognition site at the 5'-end and a PstI recognition site at the 3'-end. The PCR product was purified and digested with Bsp120I and PstI and ligated into the pICF5001 vector, which was digested with the same enzymes. Plasmid pICF5001 is a pUC18 derivative containing the modified multi cloning site 5'-GAAT-TCGGGCCCGTCGACCCTGCAGGCCCGGG-GATCCATATGCCATGGTCTAGATGAT-CATCATCACCATCATCACTAATCTAGAGAGCTCCTC-GAGGCGGCCGCGGTACCATGCATGCAAGCTT-3' (SEQ ID NO: 28). The ligation results in pICF5001 harbouring the left flanking region. The ribosomal binding site of gene 10 from phage T7 and an N-terminal fusion tag enhancing translation activity was introduced by inserting the synthetic nucleotide sequence 5'-CTGCAGGATCCTATAGG-GAGACCACAACGGTTTCCCTCTAGTAATAATTTTGT-TTAACTTTAAGAAGGAGATATACATATG-GCTAGCATTTCCATGG-3' (SEQ ID NO: 29) between the PstI and NcoI site of pICF5001 harbouring the left flanking region. The resulting vector was digested with NcoI and HindIII. The N-terminal fragment of uldA was amplified from E. coli DNA with modifying primers 5'-CATGCCATG-GTCCGTCCTGTAGAA-3' (SEQ ID NO: 30) and 5'-GC-CAAGCTTGTACAGTTCTTTCGGCTTGTTGCCC-3' (SEQ ID NO: 31), introducing a NcoI recognition site at the 5'-end and a HindIII recognition site at the 3'-end. The PCR product was purified and digested with NcoI and HindIII. The PCR product was then inserted into the vector, digested with the same enzymes, resulting in pICF 1033.

Modular vector pICF1034 contains the ribosomal binding site of gene 10 from phage T7, the complete uidA reporter gene, a second synthetic ribosomal binding site, the aadA marker gene and the right flanking region.

The ribosomal binding site of gene 10 from phage T7 was introduced into pICF5001 as described above. Modifying primers 5'-CATGCCATGGTCCGTCCTGTAGAA-3' (SEQ ID NO: 32) and 5'-CTGGGTACCTTATTGTTTGCCTC-CCTGCTGCG-3' (SEQ ID NO: 33) were used to amplify the complete uidA gene, while introducing a NcoI recognition site at the 5'-end and a KpnI recognition site at the 3'-end. The PCR product was digested with NcoI and KpnI and legated into the vector containing the T7 ribosomal binding site, digested with the same enzymes. The aadA sequence from E. coli was amplified from plasmid pFaadAII (Koop et al., 1996) with the modifying primers 5'-GGATCCATGCGT-GAAGCGGTTATCGCCG-3' (SEQ ID NO: 34) and 5'-GGT-GATGATGATCCTTGCCAACTACCTTAGTGATCTC-3' (SEQ ID NO: 35). The PCR product was reamplified with modifying primers 5'-GGGGTACCAGTTGTAGG-GAGG-GATCCATGCGTGAAGC-3' (SEQ ID NO: 36) and 5'-GCTCTAGATTAGTGATGATGGTGATGAT-GATCCTTGCC-3' (SEQ ID NO: 37) to introduce a His-tag and XbaI recognition site at the 3'-end and a synthetic ribosomal binding site and KpnI recognition site at the 5'-end. The PCR product was purified and digested with KpnI and XbaI. The right flanking region was amplified from tobacco plastid DNA (complementary to bp 155370 to bp 533 of the N. tabacum plastome) with modifying primer 5'-CTAATCTA-GAGAGCTCGTCTATAGGAGGTTTTGAAAAG -3' (SEQ ID NO: 38), introducing a XbaI recognition site at the 5'-end and exact primer 5'-CCAGAAAGAAGTATGCTTTGG-3' (SEQ ID NO: 39 , binding behind a HindIII restriction site in the tobacco plastome. The PCR product was purified and digested with XbaI and HindIII. The vector containing the T7 ribosomal binding site and uldA gene was digested with KpnI and HindIII and then legated with the two PCR products (digested with KpnI/XbaI resp. XbaI/HindIII), resulting in vector pICF1034.

12.5 µg of vector pICF1033 and 12.5 µg of vector pICF1034 were mixed, loaded on gold particles and transformed into N. tabacum plastids by particle bombardement as described in Mühlbauer et al, 2002. Selection of transformants was based on the resistance to the antibiotics spectinomycin/streptomycin, conferred by the aadA gene product. In order to amplify transformed plastid genomes and to eliminate wild-type genomes, the primary transformants (cycle-0) were subjected to several additional rounds of regeneration (from small leaf explants) on selective media containing spectinomycin (here designated as cycle-I, cycle-II etc). Correct integration of both vectors resulting in one continuous integrated region within the tobacco plastome was confirmed by PCR.

Example 4

Plastid Transformation of *Solanum tuberosum* Using Modular Vectors

In addition to tobacco the modular vector system can also be used with other important crop species. This example illustrates efficient plastid transformation in potato (*Solanum tuberosum*) following particle bombardment of protoplast-derived micro colonies using the vectors described in Example 2. Due to the high degree of homology between the plastomes of tobacco and potato the vectors containing tobacco flanking sequences can also be used for tobacco.

Plants of *S. tuberosum* cv. Walli were grown in vitro as sterile shoot cultures (20±1° C., 16 h day, light intensity 75±10 µmoles/m$^2$/sec). New cultures were initiated every 2 months by transferring shoot tips (approx. 2 cm in length) to MS medium (Murashige and Skoog, 1962) in glass tubes (2.5×20 cm). Young fully expanded leaves were selected from 3-4 week old plants and used for protoplast isolation. Leaves were cut into 1 mm stripes with a scalpel and preplasmolysed in 10 ml of MMM-550 medium. MMM-550 medium contains 4.066 g/l $MgCl_2 6H_2O$, 1.952 g/l 2(N-morpholino) ethanesulfonic acid (MES) and ~86 g/l mannitol (adjusted to 550 mOsm and pH 5.8). After 1 hour of incubation in the dark the MMM-550 was removed and replaced with 10 ml of MMS-550 medium containing 0.4% w/v Macerozyme R10 and 0.4% Cellulase R10. MMS-550 medium contains 4.066 g/l $MgCl_2.6H_2O$, 1.952 g/l MES and ~150 g/l sucrose (adjusted to 550 mOsm and pH 5.8). The leaf explants in enzyme solution were incubated for 16 hours in the dark at 25° C. without shaking. The following day the digestion was filtered through a 100 µm sieve into a centrifuge tube and then carefully overlaid with 2 ml of MMM-550 medium and centrifuged (10 min, 70 xg). Intact protoplasts were collected from the band at the interface and washed once by resuspending in 10 ml of potato protoplast culture medium followed by centrifugation (10 min, 50 xg). The protoplast culture medium contains 133.75 mg/l $NH_4Cl$, 950 mg/l $KNO_3$, 220 mg/A $CaCl_2 2H_2O$, 185 mg/A $MgSO_4 7H_2O$, 85 mg/l $KH_2PO_4$, B5 microelements (Gamborg et al. 1968), MS FE-EDTA (Murashige and Skoog, 1962), 100 mg/l myo-inositol, 100 mg/l glutamine, 100 mg/l casein hydrolysate, 1 mg/l nicotinic acid, 10 mg/l thiamine hydrochloride, 1 mg/l pyridoxine hydrochloride, 250 mgA xylose, 975 mg/l MES, 2 mg/l naphthalene acetic acid (NAA), 0.2 mg/l 2,4-dichlorophenoxyacetic acid (2,4-D), 0.5 mg/l 6-benzylaminopurine (BAP) and ~94 g/l glucose (adjusted to 550 mOsm and pH 5.8). Protoplasts were counted and resuspended at 2× the required final plating density in protoplast culture medium (2.0×10$^5$/ml) and mixed with an equal volume of 1.2% w/v alginic acid prepared in MMM-550 medium. Thin alginate layer culture in polypropylene grids was made as described in Dovzhenko et al. (1998). Following solidification of the alginate matrix, grids were cultured in 5 cm Petri dishes containing 2 ml of protoplast culture medium. Protoplasts were incubated for one day in the dark (26±1° C.) and then transferred to standard culture room conditions for further development (26±1° C., 16 h day, light intensity 75±10 μmoles/m²/sec).

12 to 15 days after embedding the grids containing potato micro colonies (approx. 8 cells) were transferred to 9 cm dishes containing SH-1 medium solidified with 0.4% w/v Gelrite. SH-1 medium contains 267.5 mg/l NH$_4$Cl, 1900 mg/l KNO$_3$, 440 mg/l CaCl$_2$2H$_2$O, 370 mg/l MgSO$_4$.7H$_2$O, 170 mg/l KH$_2$PO$_4$, MS microelements and Fe-EDTA (Murashige and Skoog, 1962), Nitsch vitamins (Nitsch and Nitsch, 1969), 40 mgA adenine sulphate, 100 mg/l casein hydrolysate, 975 mg/l MES, 0.1 mg/l NAA, 0.5 mg/l BAP, 10 g/l sucrose and 50 g/l mannitol (adjusted to pH 5.8). Two days after plating on solid medium protoplast-derived colonies were bombarded with aliquots of gold loaded with 12.5 μg of vector plCF742 and 12.5 μg of vector plCF743 using the particle coating and bombardment conditions described in Mühlbauer et al. (2002). Construction of the modular vectors plCF742 and plCF743 has been described previously (example 2). Selection of transformants was based on the resistance to the antibiotic spectinomycin, conferred by the aadA gene product. One day after bombardment, grids were transferred to dishes containing Gelrite-solidified SH-1 medium+500 mg/l spectinomycin and subcultured every 3 weeks to fresh selection dishes. Plastid transformants were observed as green micro colonies following 8-12 weeks of selection (non-transformed tissues are bleached on SH-1 medium containing spectinomycin). Individual colonies (approx. 1 mm in diameter) were transferred to 5 cm dishes containing SH-1 medium+100 mg/l spectinomycin. For regeneration calli (approx. 5 mm in diameter) were transferred to SH-2 medium solidified with 0.4% w/v Gelrite containing 100 mg/l spectinomycin. SH-2 medium is identical to SH-1 medium (see above) except that the NAA is replaced with 0.1 mg/l indole-3-acetic acid (IAA), BAP is replaced with 1 mg/l zeatin and the mannitol content is reduced from 50 g/l to 36 g/l. Shoots were removed from regenerating calli after 6-8 weeks of culture on SH-2 medium these were transferred to antibiotic-free MS medium for rooting and further development.

Spectinomycin resistant potato shoots were analysed by PCR to verify correct plastid transformation. Three different primer pairs were used as described for the analysis of tobacco transformants (example 2):

A) 5'-CAGACTAATACCAATCCAAGCC-3' (SEQ ID NO: 20) (binding outside the left flanking region within the *S. tuberosum* plastome) and 5'-CTATCAGAGGTAGTTG-GCGTC-3' (SEQ ID NO: 21) (binding within the aadA marker gene).

B) 5'-CACTACATTTCGCTCATCGCC-3' (SEQ ID NO: 22) (binding within the aadA marker gene) and 5'-TATTC-CGACTTCCCCAGAGC-3' (SEQ ID NO: 23) (binding outside the right flanking region within the *S. tuberosum* plastome)

C) 5'-CATCAATACCTCGGTCTAG-3' (SEQ ID NO: 24) (binding within the left flanking region) and 5'-ACACAT-AGTATGCCCGGTC-3' (SEQ ID NO: 25) (binding within the right flanking region).

Correct integration of both vectors resulting in one continuous integrated region within the potato plastome was shown by PCR using the three primer pairs described above.

References

Koop et al., 1996, *Planta* 199, 193-201

Dovzhenko, A., Bergen, U. & Koop, H. U. Thin-alginate-layer technique for protopalst culture of tobacco leaf protoplasts: shoot formation in less than two weeks. *Protoplasma* 204, 114-118 (1998).

Galvin S. B., 1998, *Curr. Opin. Biotechnol.*, 9, 227-232.

Gamborg, O. L., Miller, R. A. & Ojima, K. Nutrient requirements of suspension cultures of soybean root cells. *Exp Cell Res* 50, 151-158 (1968).

Gray M. W., Origin and Evolution of Plastid Genomes and Genes, in: Bogorad L. and Vasil I. K. (eds.), Cell Culture and Somatic Cell Genetics of Plants, Volume 7A, Academic Press, San Diego, 1991.

Heifetz, P., 2000, *Biochimie,* 82, 655-666.

Huang F.-C., Klaus S., Herz S., Koop H-U., Golds T., 2002, *MGG*, in press.

Iamtham and Day, 2000, *Nat. Biotechnol.*, 18, 1172-1176.

Nitsch, J. P. and Nitsch, C. Haploid plants from pollen grains. Science 169, 85 (1969).

Marechal-Drouard L., Kuntz M., Weil J. H., tRNAs and tRNA Genes of Plastids, in: Bogorad L. and Vasil I. K. (eds.), Cell Culture and Somatic Cell Genetics of Plants, Volume 7A, Academic Press, San Diego, 1991.

Mühlbauer S., Lössl A., Tzekova L, Zhou Z., Koop H.-U., 2002, *Plant J.* 32, 175-184 (2002).

Murashige, T. & Skoog, F. A revised medium for rapid growth and bioassays with tobacco tissue cultures. *Physiol Plant* 15, 473-497 (1962).

Palmer J. D., *Plastid Chromosomes: Structure and Evolution*, in: *Bogorad L.* and *Vasil I. K.* (eds.), *Cell Culture and Somatic Cell Genetics of Plants*, Volume 7A, Academic Press, San Diego, 1991.

The Arabidopsis Genome Initiative, 2000, *Nature,* 408, 796-815.

Svab, Z., Hajdukiewicz, P., and Maliga, P., 1990, *Proc. Natl. Acad. Sci. USA* 87, 8526-8530.

Zou Z., 2001, PhD thesis, Ludwig-Maximilians-Universitat, Munich, Germany.

U.S. Pat. No. 5,877,402

U.S. Pat. No. 5,451,513

The invention claimed is:

1. A process of generating transgenic plants or plant cells transformed on their plastome, comprising (a) introducing into plant plastids a first DNA molecule and a second DNA molecule, wherein said first DNA molecule contains a first region homologous to a region of the plastome for directing plastome integration and a first sequence of interest, wherein said first DNA molecule contains only one region homologous to a region of the plastome for directing plastome integration, and said second DNA molecule contains a second region homologous to a region of the plastome for directing plastome integration and a second sequence of interest, whereby a sequence segment of said first sequence of interest is homologous to a sequence segment of said second sequence of interest, wherein said first and said second DNA molecules are introduced into said plant plastids by co-transformation, and (b) selecting transformants having an integration sequence stably integrated in the plastome, whereby said integration sequence contains at least a portion of said first and at least a portion of said second sequence of interest as a continuous sequence.

2. The process according to claim 1, wherein said first and said second sequences of interest are different from each other.

3. The process according to claim 1, wherein said first and said second sequences of interest each contains a further sequence in addition to said sequence segment.

4. The process according to claim 1, wherein one or more additional DNA molecules are introduced into said plant plastids in addition to said first and said second DNA molecule, whereby said additional DNA molecule(s) comprise(s) additional sequence(s) of interest.

5. The process according to claim 4, wherein said additional DNA molecule(s) contain(s) a sequence segment homologous to a sequence segment of said first sequence of interest and a sequence segment homologous to said second sequence of interest.

6. The process according to claim 1, wherein said first and/or said second sequence of interest contains one or more genes of interest or fragments of a gene of interest.

7. The process according to claim 6, wherein a gene of interest is split into two or more fragments and wherein said first and/or said second sequence of interest contains a fragment of said gene of interest, whereby said gene of interest is assembled from said two or more fragments upon formation of said integration sequence.

8. The process according to claim 6, wherein said gene of interest is a selectable marker gene.

9. The process according to claim 8, wherein said selectable marker gene is aphA-6.

10. The process according to claim 1, wherein said first sequence of interest contains a 5' part of a gene of interest and said second sequence of interest contains a 3' part of said gene of interest and said integration sequence contains said gene of interest such that it can be expressed.

11. The process according to claim 1, wherein said first sequence of interest contains a 5' part of a gene of interest and said second sequence of interest contains a 3' part of said gene of interest, wherein said first sequence of interest contains upstream of said 5' part of said gene of interest a sequence element homologous to a sequence element located downstream of said 3' part of said gene of interest of the second sequence of interest, whereby said sequence elements enable excision by homologous recombination of a part of said integration sequence that comprises said 5' and/or said 3' part of said gene of interest.

12. The process according to claim 1, wherein said first or said second DNA molecule contains a selectable marker gene outside of a sequence unit consisting of the region homologous to a region of the plastome and the sequence of interest, for allowing loss of said marker gene.

13. The process according to claim 1, wherein a selectable marker gene is split into a first and a second fragment, whereby said first fragment is incorporated in said first DNA molecule outside of a first sequence unit and said second fragment is incorporated in said second DNA molecule outside of a second sequence unit, whereby said first sequence unit consists of said first homologous region and said first sequence of interest and said second sequence unit consists of said second homologous region and said second sequence of interest.

14. The process according to claim 1, wherein said first and said second DNA molecule each contain only one region homologous to a region of the plastome for directing plastome integration.

15. The process according to claim 1, wherein said first and said second homologous region together correspond to a continuous sequence of the plastome to be transformed.

16. The process according to claim 1, wherein homoplastomic transgenic plants are regenerated from said transformants.

17. A kit-of-parts comprising a first and a second DNA molecule, wherein said first DNA molecule contains a first region homologous to a region of the plastome for directing plastome integration and a first sequence of interest, wherein said first DNA molecule contains only one region homologous to a region of the plastome for directing plastome integration, and said second DNA molecule contains a second region homologous to a region of the plastome for directing plastome integration and a second sequence of interest, whereby a sequence segment of said first sequence of interest is homologous to a sequence segment of said second sequence of interest.

18. A plant or plant cell transformed a first and a second DNA molecule, wherein said first DNA molecule contains a first region homologous to a region of the plastome for directing plastome integration and a first sequence of interest, wherein said first DNA molecule contains only one region homologous to a region of the plastome for directing plastome integration, and said second DNA molecule contains a second region homologous to a region of the plastome for directing plastome integration and a second sequence of interest, whereby a sequence segment of said first sequence of interest is homologous to a sequence segment of said second sequence of interest.

19. A plant or plant cell obtained according to a process comprising (a) introducing into plant plastids a first DNA molecule and a second DNA molecule, wherein said first DNA molecule contains a first region homologous to a region of the plastome for directing plastome integration and a first sequence of interest, wherein said first DNA molecule contains only one region homologous to a region of the plastome for directing plastome integration, and said second DNA molecule contains a second region homologous to a region of the plastome for directing plastome integration and a second sequence of interest, whereby a sequence segment of said first sequence of interest is homologous to a sequence segment of said second sequence of interest, wherein said first and said second DNA molecules are introduced into said plant plastids by co-transformation, and (b) selecting transformants having an integration sequence stably integrated in the plastome, whereby said integration sequence contains at least a portion of said first and at least a portion of said second sequence of interest as a continuous sequence.

20. A seed obtained from a plant, said plant obtained according to a process comprising
   (a) introducing into plant plastids a first DNA molecule and a second DNA molecule, wherein said first DNA molecule contains a first region homologous to a region of the plastome for directing plastome integration and a first sequence of interest, wherein said first DNA molecule contains only one region homologous to a region of the plastome for directing plastome integration, and said second DNA molecule contains a second region homologous to a region of the plastome for directing plastome integration and a second sequence of interest, whereby a sequence segment of said first sequence of interest is homologous to a sequence segment of said second sequence of interest, wherein said first and said second DNA molecules are introduced into said plant plastids by co-transformation, and
   (b) selecting transformants having an integration sequence stably integrated in the plastome, whereby said integration sequence contains at least a portion of said first and at least a portion of said second sequence of interest as a continuous sequence.

21. A process of generating transgenic plants or plant cells transformed on their plastome, comprising
   (a) introducing into plant plastids a first DNA molecule and a second DNA molecule, wherein said first DNA molecule contains a first region homologous to a region of the plastome for directing plastome integration and a first sequence of interest, and said second DNA molecule contains a second region homologous to a region of the plastome for directing plastome integration and a second sequence of interest, whereby a sequence segment of said first sequence of interest is homologous to a sequence segment of said second sequence of interest, wherein said first and said second DNA molecules are introduced into said plant plastids by co-transformation, and
   (b) selecting transformants having an integration sequence stably integrated in the plastome, whereby said integration sequence contains at least a portion of said first and at least a portion of said second sequence of interest as a continuous sequence.

22. A process of generating transgenic plants or plant cells transformed on their plastome, comprising
   (a) introducing into plant plastids a first DNA molecule and a second DNA molecule, wherein said first DNA molecule contains a first region homologous to a region of the plastome for directing plastome integration and a first sequence of interest, and said second DNA molecule contains a second region homologous to a region of the plastome for directing plastome integration and a second sequence of interest, whereby a sequence segment of said first sequence of interest is homologous to a sequence segment of said second sequence of interest, and wherein said first and said second DNA molecules each contains only one region homologous to a region of the plastome for directing plastome integration, and
   (b) selecting transformants having an integration sequence stably integrated in the plastome, whereby said integration sequence contains at least a portion of said first and at least a portion of said second sequence of interest as a continuous sequence.

23. A process of generating transgenic plants or plant cells transformed on their plastome, comprising
   (a) introducing into plant plastids a first DNA molecule and a second DNA molecule, wherein said first DNA molecule contains a first region homologous to a region of the plastome for directing plastome integration and a first sequence of interest, wherein said first DNA molecule contains only one region homologous to a region of the plastome for directing plastome integration, and said second DNA molecule contains a second region homologous to a region of the plastome for directing plastome integration and a second sequence of interest, whereby a sequence segment of said first sequence of interest is homologous to a sequence segment of said second sequence of interest, wherein said first sequence of interest contains a 5' part of a gene of interest and said second sequence of interest contains a 3' part of said gene of interest, wherein said first sequence of interest contains upstream of said 5' part of said gene of interest a sequence element homologous to a sequence element located downstream of said 3' part of said gene of interest of the second sequence of interest, whereby said sequence elements enable excision by homologous recombination of a part of said integration sequence that comprises said 5' and/or said 3' part of said gene of interest, and
   (b) selecting transformants having an integration sequence stably integrated in the plastome, whereby said integration sequence contains at least a portion of said first and at least a portion of said second sequence of interest as a continuous sequence.

\* \* \* \* \*

UNITED STATES PATENT AND TRADEMARK OFFICE
CERTIFICATE OF CORRECTION

PATENT NO. : 7,528,292 B2
APPLICATION NO. : 10/523474
DATED : May 5, 2009
INVENTOR(S) : Herz et al.

It is certified that error appears in the above-identified patent and that said Letters Patent is hereby corrected as shown below:

Column 3,
Line 18, "hormoplastomic" should read --homoplastomic--.

Column 22,
Lines 45 and 59, "legated" should read --ligated--.

Column 23,
Lines 35 and 46, "legated" should read --ligated--.

Column 25,
Line 61, "legated" should read --ligated--.

Signed and Sealed this

Eleventh Day of August, 2009

David J. Kappos
*Director of the United States Patent and Trademark Office*